US011643317B2

(12) United States Patent
Hayakawa et al.

(10) Patent No.: US 11,643,317 B2
(45) Date of Patent: May 9, 2023

(54) ASEPTIC FILLING METHOD AND ASEPTIC FILLING APPARATUS

(71) Applicant: Dai Nippon Printing Co., Ltd., Tokyo (JP)

(72) Inventors: Atsushi Hayakawa, Tokyo (JP); Yuiko Wada, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 594 days.

(21) Appl. No.: 16/493,069

(22) PCT Filed: Apr. 6, 2018

(86) PCT No.: PCT/JP2018/014697
§ 371 (c)(1),
(2) Date: Sep. 11, 2019

(87) PCT Pub. No.: WO2018/186484
PCT Pub. Date: Oct. 11, 2018

(65) Prior Publication Data
US 2021/0107780 A1    Apr. 15, 2021

(30) Foreign Application Priority Data

Apr. 7, 2017  (JP) .............................. JP2017-076440

(51) Int. Cl.
*B67C 7/00*  (2006.01)
*B67C 3/22*  (2006.01)
(Continued)

(52) U.S. Cl.
CPC .............. *B67C 7/0073* (2013.01); *A61L 2/07* (2013.01); *A61L 2/087* (2013.01); *A61L 2/10* (2013.01);
(Continued)

(58) Field of Classification Search
CPC ........... B65B 55/02; B65B 55/04; B67C 3/00; B67C 7/00; B29C 49/42
(Continued)

(56) References Cited

U.S. PATENT DOCUMENTS 6,562,281 B1     5/2003  Marchau et al.
2005/0118057 A1*  6/2005  Quetel ...................... A61L 2/10
                                                422/302
(Continued)

FOREIGN PATENT DOCUMENTS

EP    2 3 94 950 A1    12/2011
EP    3 069 846 A1     9/2016
(Continued)

OTHER PUBLICATIONS

Extended European Search Report (Application No. 18781453.8) dated Jan. 11, 2021.
(Continued)

*Primary Examiner* — Andrew M Tecco
*Assistant Examiner* — Jacob A Smith
(74) *Attorney, Agent, or Firm* — Burr Patent Law, PLLC

(57) ABSTRACT

To make a sterilization step appropriate in an aseptic filling apparatus. Provided is an aseptic filling apparatus including a step of sterilizing a preform and a step of sterilizing a container obtained by molding the preform, wherein assuming sterilization effects in the respective sterilization steps as X [LRV] and Y [LRV], a relationship of $5 \leq X+Y \leq 10$ (where $Y \geq 0$) is established.

6 Claims, 10 Drawing Sheets

(51) Int. Cl.
  *B29C 49/42*    (2006.01)
  *A61L 2/07*     (2006.01)
  *A61L 2/08*     (2006.01)
  *A61L 2/10*     (2006.01)
  *A61L 2/18*     (2006.01)
  *B29C 49/46*    (2006.01)
  *B29L 31/00*    (2006.01)

(52) U.S. Cl.
  CPC .......... *A61L 2/186* (2013.01); *B29C 49/4252* (2013.01); *B29C 49/4273* (2013.01); *B29C 49/46* (2013.01); *B67C 3/225* (2013.01); *B67C 7/0046* (2013.01); *A61L 2202/23* (2013.01); *B29C 49/42414* (2022.05); *B29L 2031/7158* (2013.01); *B67C 2003/227* (2013.01); *B67C 2003/228* (2013.01); *B67C 2007/006* (2013.01); *B67C 2007/0066* (2013.01)

(58) Field of Classification Search
  USPC .......................................................... 53/426
  See application file for complete search history.

(56)               References Cited

U.S. PATENT DOCUMENTS

2008/0152538 A1*  6/2008  Quetel ................... A61L 2/208
                                                      422/291
  2011/0061343 A1   3/2011  Roithmeier et al.
  2011/0094616 A1   4/2011  Hayakawa et al.
  2012/0288406 A1  11/2012  Iwashita et al.
  2014/0144105 A1   5/2014  Hayakawa et al.
  2016/0325482 A1  11/2016  Hayakawa et al.

FOREIGN PATENT DOCUMENTS

EP       3 069 847 A1    9/2016
  JP       2001-510104 A1  7/2001
  JP       2006-111295 A1  4/2006
  JP       2010036973 A  *  8/2008  ............. A61L 2/087
  JP       2009-274740 A1 11/2009
  JP       2009-280222 A1 12/2009
  JP       2010-036973 A1  2/2010
  JP       2010036973 A  *  2/2010  ............. A61L 2/087
  JP       2010051338 A  *  3/2010  ............ B67C 7/0073
  JP       2010-155631 A1  7/2010
  JP       2010-235209 A1 10/2010
  JP       2010235209 A  * 10/2010  ............... A61L 2/07
  JP       2011-056943 A1  3/2011
  JP       2011-147673 A1  8/2011
  JP       2013-035561 A1  2/2013
  JP       2013-233979 A  11/2013
  JP       2013233979    * 11/2013  ............. B65B 55/04
  JP       2016-190500 A1 11/2016
  WO       2010/016539 A1  2/2010
  WO       2010/090247 A1  8/2010

OTHER PUBLICATIONS

International Search Report and Written Opinion (Application No. PCT/JP2018/014697) dated Jun. 19, 2018.

* cited by examiner

PREFORM SUPPLY

STERILIZER GAS BLASTING

HEATING

BLOW MOLDING

ASEPTIC FILLING METHOD AND ASEPTIC FILLING APPARATUS

BACKGROUND OF THE INVENTION

1. Field of the Invention

The present invention relates to an aseptic filling method and an aseptic filling apparatus for a beverage or the like where a preform is heated, the heated preform is molded into a container, the molded container is filled with sterilized contents, such as a beverage, and the container filled with the contents is sealed by a sterilized lid member, wherein the preform is sterilized, and the molded container from the sterilized preform is sterilized.

2. Description of Related Art

Conventionally, an aseptic filling method has been proposed which is an in-line system where a sterilizer, such as hydrogen peroxide, is blasted to a preform while the preform is conveyed and, then, the preform is heated so as to activate the sterilizer adhering to the surface and, at the same time, the preform is heated to a molding temperature and, thereafter, the heated preform is molded into a bottle by a blow-molding machine, the molded bottle is filled with a beverage or the like, and the bottle is capped, thus obtaining an aseptic package (Patent Literatures 1, 2).

An aseptic filling method is also proposed where a preform is heated to a molding temperature, the heated preform is molded into a container, the molded container is sterilized, the sterilized container is filled with sterilized contents in an aseptic atmosphere, and the container filled with the contents is sealed by a sterilized lid member (Patent Literatures 3, 4).

A method where a preform is sterilized requires smaller sterilization area than a method where a container is sterilized. Accordingly, the method where a preform is sterilized uses a smaller amount of sterilizer, and requires a shorter sterilization time, thus having greater advantage. However, there is a possibility that a sterilized preform is contaminated with bacteria and the like in a preform heating step where the sterilized preform is heated to a molding temperature, a molding step where the heated preform is molded into a container, and an inspection step where the molded container is inspected. The reason is as follows. Devices and equipment used in the heating step, the molding step, and the inspection step are required to be sterilized before an aseptic filling apparatus is operated. However, packings which may be deteriorated by a sterilizer are used, and it is difficult to sterilize oil used in a sliding portion and hence, the devices and equipment used in the heating step, the molding step, and the inspection step cannot be completely sterilized. There is also proposed a method for sterilizing a heating unit and a molding unit including such devices and equipment which are difficult to be completely sterilized. However, such a method is not sufficient (Patent Literatures 5, 6).

Accordingly, an aseptic filling apparatus where a molded container is sterilized has higher reliability than an aseptic filling apparatus where a preform is sterilized. In view of the above, an aseptic filling method is also proposed where a preform is pre-sterilized, the pre-sterilized preform is heated to a molding temperature, the heated preform is molded into a container, the molded container is subjected to main sterilization, the container which is subjected to main sterilization is filled with sterilized contents in an aseptic atmosphere, and the container filled with the contents is sealed by a sterilized lid member (Patent Literatures 7, 8).

CITATION LIST

Patent Literature

Patent Literature 1: Japanese Patent Laid-Open No. 2001-510104
Patent Literature 2: Japanese Patent Laid-Open No. 2009-274740
Patent Literature 3: Japanese Patent Laid-Open No. 2006-111295
Patent Literature 4: Japanese Patent Laid-Open No. 2010-155631
Patent Literature 5: Japanese Patent Laid-Open No. 2011-147673
Patent Literature 6: Japanese Patent Laid-Open No. 2016-190500
Patent Literature 7: Japanese Patent Laid-Open No. 2010-235209
Patent Literature 8: Japanese Patent Laid-Open No. 2013-035561

SUMMARY OF INVENTION

Technical Problem

In the aseptic filling apparatus where a container molded from a preform is sterilized, container is sterilized and, thereafter, the container is filled with the contents in a state where asepticity in the container and the atmosphere is maintained. Accordingly, the aseptic filling apparatus where a container molded from a preform is sterilized has higher reliability in asepticity than an aseptic filling apparatus where a preform is sterilized. However, the aseptic filling apparatus where a preform is sterilized is allowed to have a smaller size than the aseptic filling apparatus where a container is sterilized. Accordingly, the aseptic filling apparatus where a preform is sterilized requires lower initial capital investment, and a smaller sterilization area and hence, it is possible to suppress running cost. In view of the above, the aseptic filling apparatus is proposed which sterilizes a preform, and also sterilizes a container obtained by molding the preform. In such an aseptic filling apparatus, the size of a sterilizer apparatus for a container can be reduced compared with the aseptic filling apparatus where a container is sterilized and hence, the size of the aseptic filling apparatus as a whole can be also reduced, thus requiring smaller installation area. Further, compared with the aseptic filling apparatus where a preform is sterilized, such an aseptic filling apparatus has higher reliability in asepticity.

However, the aseptic filling apparatus where both a preform and a container are sterilized has a sterilizing power equal to or higher than a required level of asepticity so that such an aseptic filling apparatus becomes excessive compared with an appropriate facility. Further, sterilization is also performed more than necessary and hence, unnecessary running cost may be required. Therefore, there is the following demand. In the aseptic filling apparatus where a preform and a container are sterilized, sterilization is performed under appropriate sterilization conditions corresponding to required sterilizing power, and such an aseptic filling apparatus includes an appropriate sterilizer apparatus which does not perform excessive sterilization.

It is an object of the present invention to solve the above-mentioned problems. That is, it is an object of the present invention to provide an aseptic filling apparatus and an aseptic filling method which includes a step of sterilizing a preform and a step of sterilizing a container, wherein the aseptic filling method and the aseptic filling apparatus appropriately exhibit required sterilizing power, thus having higher reliability in asepticity than an aseptic filling apparatus where a preform is sterilized, and a facility has a more compact shape and requires milder sterilization conditions than an aseptic filling apparatus where a container is sterilized.

Solution to Problem

The present invention is directed to an aseptic filling method including: a preform sterilization step where a preform is sterilized; a preform heating step where the sterilized preform is heated to a molding temperature; a molding step where the heated preform is molded into a container; a container sterilization step where the molded container is sterilized; a filling step where the sterilized container is filled with sterilized contents in an aseptic atmosphere; and a sealing step where the container filled with the contents is sealed by a sterilized lid member, the preform and the container being made to continuously travel, wherein assuming sterilizing ability in the preform sterilization step as X [LRV], and sterilizing ability within a range from the preform heating step to the container sterilization step as Y [LRV], a following formula is satisfied.

$$5 \leq X + Y \leq 10$$

(where $Y \geq 0$)

In the aseptic filling method according to the present invention, it is preferable that the preform sterilization step be performed by performing any one, two or more selected from contact of a sterilizer with the preform, irradiation with electron beam to the preform, irradiation with light containing ultraviolet rays to the preform, contact of hot water with the preform, and contact of superheated steam with the preform.

In the aseptic filling method according to the present invention, it is preferable that the container sterilization step be performed by performing any one, two or more selected from contact of a sterilizer with the container, irradiation with electron beam to the container, irradiation with light containing ultraviolet rays to the container, contact of hot water with the container, and filling of the container with heated contents.

The present invention is also directed to an aseptic filling apparatus provided with a conveying path which causes a preform and a container to continuously travel until the preform is molded into the container, the container is filled with contents, and the container is sealed by a lid, the aseptic filling apparatus including: a preform sterilizing device configured to sterilize the preform; a heating unit configured to heat the sterilized preform to a molding temperature; a molding unit configured to blow-mold the preform, which is heated to the molding temperature, into the container; a container sterilizing device configured to sterilize the container which is blow molded; a filling device configured to fill the sterilized container with sterilized contents; and a sealing device configured to seal the container, which is filled with the contents, with a sterilized lid member, the preform sterilizing device, the heating unit, the molding unit, the container sterilizing device, the filling device, and the sealing device being provided along the conveying path, wherein assuming sterilizing ability of the preform sterilizing device as X [LRV], and sterilizing ability within a range from the heating unit to the container sterilizing device as Y [LRV], a following formula is satisfied.

$$5 \leq X + Y \leq 10$$

(where $Y \geq 0$)

In the aseptic filling apparatus according to the present invention, it is preferable that the preform sterilizing device perform any one, two or more selected from contact of a sterilizer with the preform, irradiation with electron beam to the preform, irradiation with light containing ultraviolet rays to the preform, contact of hot water with the preform, and contact of superheated steam with the preform.

In the aseptic filling apparatus according to the present invention, it is preferable that the container sterilizing device perform any one, two or more selected from contact of a sterilizer with the container, irradiation with electron beam to the container, irradiation with light containing ultraviolet rays to the container, contact of hot water with the container, and filling of the container with heated contents.

DETAILED DESCRIPTION OF THE INVENTION

According to the present invention, a sterilization effect on a preform and a sterilization effect on a container are made to match required sterilization effects and hence, it is possible to provide an aseptic filling method and an aseptic filling apparatus with no excessive sterilization, but with high reliability. A preform is sterilized, and a container obtained by molding the preform is further sterilized. Accordingly, it is sufficient to sterilize the container such that bacteria and the like which contaminate the preform and the container during a period after the preform is sterilized and before the container is sterilized. Therefore, a sterilizing device for containers is not excessively large in size, thus allowing the aseptic filling apparatus to have a compact shape. Further, it is not always necessary to sterilize a heating unit and a molding unit for preforms and an inspection device for containers for sterilizing the container. Accordingly, it is unnecessary to use a material which is not deteriorated by a sterilizer, and it is not always necessary to provide a sterilizing device for these devices. Further, assume case where a sterilization method is used where the same sterilizer is used in a preform sterilization step and a container sterilization step. In such a case, it is possible to use a chemical tank, an aseptic air supply device, an evacuating device, a chemical decomposition device and the like for both the preform sterilization step and the container sterilization step. Accordingly, there is no possibility of an increase in initial investment cost.

DESCRIPTION OF EMBODIMENTS

Hereinafter, an embodiment of the present invention will be described.

First, the description will be made with reference to FIG. 1 with respect to the process from the supply of a preform and the summary of an aseptic filling apparatus formed of a preform sterilizing unit; a heating unit; a molding unit; an inspection device; a container sterilizing unit; a filling unit; a sealing unit; and a discharging unit. A preform sterilization step performed in the preform sterilizing unit will be described with reference to FIG. 3, FIG. 4, FIG. 6, FIG. 7 and FIG. 8. Heating and blow molding step of the preform will be described with reference to FIG. 10 and FIG. 11. A sterilization step for a container will be described with reference to FIG. 13 and FIG. 14. A filling step and a sealing step will be described with reference to FIG. 15 and FIG. 16. According to the aseptic filling method and the aseptic filling apparatus of this embodiment, it is possible to obtain an advantageous effect of reducing a running cost under appropriate sterilization conditions and an advantageous effect of reducing initial capital investment brought about by the usage of a device with an appropriate scale. As a result, preforms and containers are sterilized under appropriate conditions using appropriate devices and hence, it is possible to acquire aseptic fill products with high reliability without performing excessive sterilization.

(Summary of Aseptic Filling Method and Aseptic Filling Apparatus)

Figure 1:
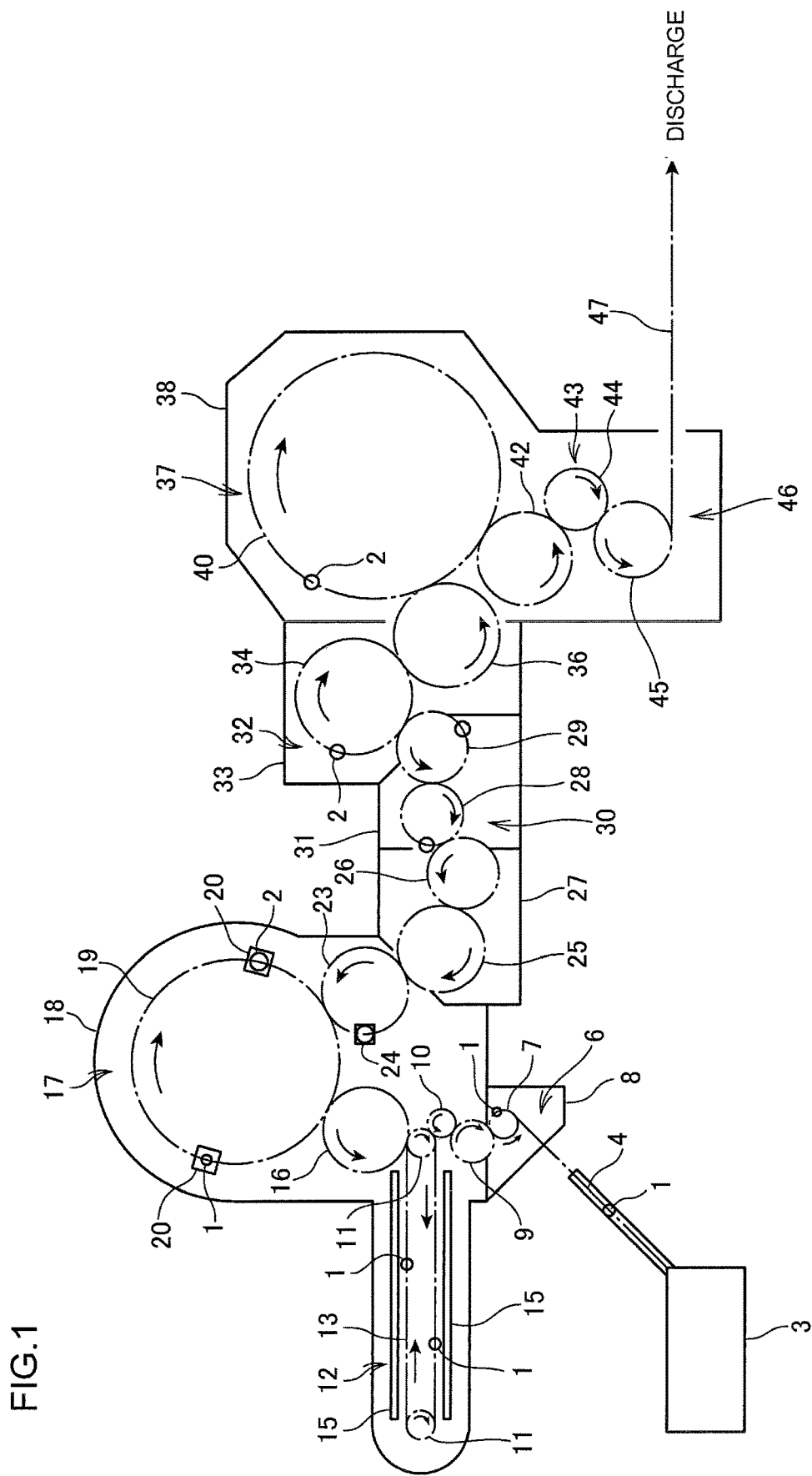
FIG. 1 is a plan view showing a schematic configuration of one example of an aseptic filling apparatus according to an embodiment of the present invention.

As shown in FIG. 1, the aseptic filling apparatus according to this embodiment includes: a preform supply device 3 which supplies preforms 1; a preform sterilizing unit 6 which sterilizes each preform; a heating unit 12 which heats the preform 1 to a temperature at which the preform 1 is molded into a container 2; a molding unit 17 which molds the heated preform 1 into the container 2; a container sterilizing unit 30 which sterilizes the molded container 2; an air rinsing unit 32 which performs air rinsing on the sterilized container 2; a filling unit 37 which fills the air-rinsed container 2 with sterilized contents; and a sealing unit 43 which seals the container 2, which is filled with the contents, with a sterilized cap 41. The aseptic filling apparatus further includes a discharging unit 46 where the sealed container 2 is placed on a discharging conveyor 47, and from which the container 2 is discharged to a non-aseptic zone. It is not always necessary to provide the air rinsing unit 32.

The preform sterilizing unit 6 is shielded by a preform sterilizing unit chamber 8. The heating unit 12 and the molding unit 17 are shielded by a molding unit chamber 18. The container sterilizing unit 30 is shielded by a container sterilizing unit chamber 31. The air rinsing unit 32 is shielded by an air rinsing unit chamber 33. The filling unit 37, the sealing unit 43, and the discharging unit 46 are shielded by a filling unit chamber 38. Depending on a method for sterilizing the container sterilizing unit 30, a gas or mist of a sterilizer or a mixture thereof, or ozone is generated in the container sterilizing unit chamber 31. To prevent the gas or mist of a sterilizer or a mixture thereof, or ozone from flowing into the molding unit 17, an atmosphere shut-off chamber 27 is provided between the molding unit 17 and the container sterilizing unit 30. The atmosphere shut-off chamber 27 is evacuated so that there is no possibility that a gas or mist of a sterilizer or a mixture thereof, or ozone which is generated in the container sterilizing unit 30 flows into the molding unit 17. Also in the preform sterilizing unit 6, a gas or mist of a sterilizer or a mixture thereof or ozone is generated depending on a sterilization method. Accordingly, such a gas or the like is evacuated via a processing device which makes the gas or the like harmless. Such a processing device is also used in evacuating the inside of the atmosphere shut-off chamber 27.

Before the operation of the aseptic filling apparatus is started, the inside of each of the container sterilizing unit chamber 31, the air rinsing unit chamber 33 and the filling unit chamber 38 are sterilized. A single-fluid spray or a twin-fluid spray, which sprays a sterilizer in the form of a mixture with compressed air, is provided to the inside of each chamber as a sterilizer blasting nozzle. The sterilizer blasting nozzle blasts a sterilizer such that the sterilizer adheres to entire area in each chamber which requires sterilization. The inside of each chamber is sterilized by the blasted sterilizer. The sterilizer blasting nozzle is disposed so as to allow a sterilizer to adhere to the entire area in each chamber. After the sterilizer is blasted, aseptic air at a room temperature or heated aseptic air is blasted to each chamber so as to activate the sterilizer remaining in each chamber, thus further removing the sterilizer. It is also possible to adopt a configuration where aseptic water is blasted to the inside of each chamber before aseptic air is blasted, thus removing a sterilizer. It is also possible to adopt a configuration where a sterilizer blasting nozzle is also provided to the inside of the molding unit chamber 18, which shields the heating unit 12, the molding unit 17 and an inspection device 24, so as to sterilize the inside of the molding unit chamber 18.

After the container sterilizing unit chamber 31, the air rinsing unit chamber 33 and the filling unit chamber 38 are sterilized, aseptic air which is brought into an aseptic state by an aseptic filter is supplied into the container sterilizing unit chamber 31, the air rinsing unit chamber 33 and the filling unit chamber 38, and the inside of each chamber is kept at a positive pressure. The inside of each chamber is kept at a positive pressure by aseptic air so that asepticity in the aseptic filling apparatus in the portions downstream of the container sterilizing unit chamber 31 is maintained. Pressures for keeping the inside of respective chambers at a positive pressure are set such that lower pressures are set for the chambers disposed toward the upstream side. That is, the filling unit chamber 38 is set at the highest pressure, and the pressures reduces in order from the air rinsing unit chamber 33 and the container sterilizing unit chamber 31. The atmosphere shut-off chamber 27 is evacuated so that the inside of the atmosphere shut-off chamber 27 is kept at a pressure substantially equal to the atmospheric pressure.

Detail of Embodiment

Figure 2:
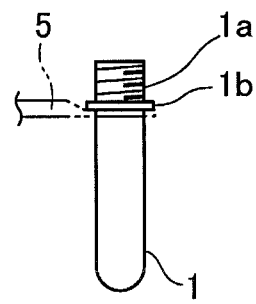
FIG. 2 shows a preform supply step according to the embodiment of the present invention.

The preform 1 shown in FIG. 2 is continuously conveyed to the preform sterilizing unit 6 from the preform supply device 3 shown in FIG. 1 by a preform supply conveyor 4 at a desired speed.

Figure 11:
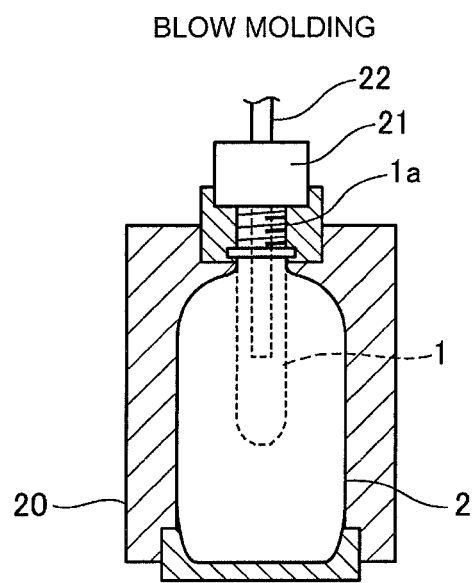
FIG. 11 shows a step of performing blow molding on the preform according to the embodiment of the present invention.

The preform 1 according to the embodiment of the present invention is a bottomed tubular body having a test tube shape, and is shown in FIG. 2. A mouth portion 1a substantially equal to that of the container 2 shown in FIG. 11 is formed on the preform 1 in the early stage of the molding of the preform 1. A male thread is formed on the mouth portion 1a of the preform 1 simultaneously with the molding of the preform 1. A support ring 1b for conveyance is also formed at the lower portion of the mouth portion 1a of the preform 1. The preform 1 or the container 2 travels through the inside of the aseptic filling apparatus in a state of being held by a gripper 5 via the support ring 1b. The preform 1 is molded by injection molding, compression molding or the like. A material for forming the preform 1 may be a thermoplastic resin, such as polyethylene terephthalate, polyethylene naphthalate, polypropylene, or polyethylene. The material for forming the preform 1 may be a single substance or a mixture of these resins, or may contain a recycled thermoplastic resin. Further, in order to impart a barrier property, the material for forming the preform 1 may contain a thermoplastic resin, such as ethylene-vinyl alcohol copolymer, or polyamide, where aromatic amine, such as m-xylenediamine, acts as a monomer, in the form of a layer or a mixture.

The preform 1 conveyed to the preform sterilizing unit 6 is conveyed to a preform sterilizing wheel 7 where a large number of grippers 5 is provided at fixed intervals, and the preform 1 is sterilized in the preform sterilizing unit 6. A sterilization step of the preform 1 is performed by any one, two or more selected from contact with a sterilizer, irradiation with electron beam, irradiation with light containing ultraviolet rays, contact with hot water, and contact with superheated steam. The preform 1 may be preheated by hot air before the preform 1 is sterilized. To preheat the preform 1, a wheel for preheating may be provided on the upstream side of the preform sterilizing wheel 7. Preheating the preform 1 enhances a sterilization effect.

Figure 3:
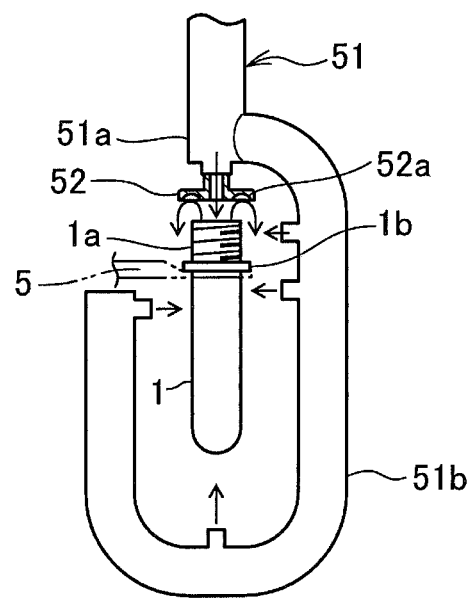
FIG. 3 shows a step of blasting a sterilizer gas to a preform according to the embodiment of the present invention.
Figure 4:
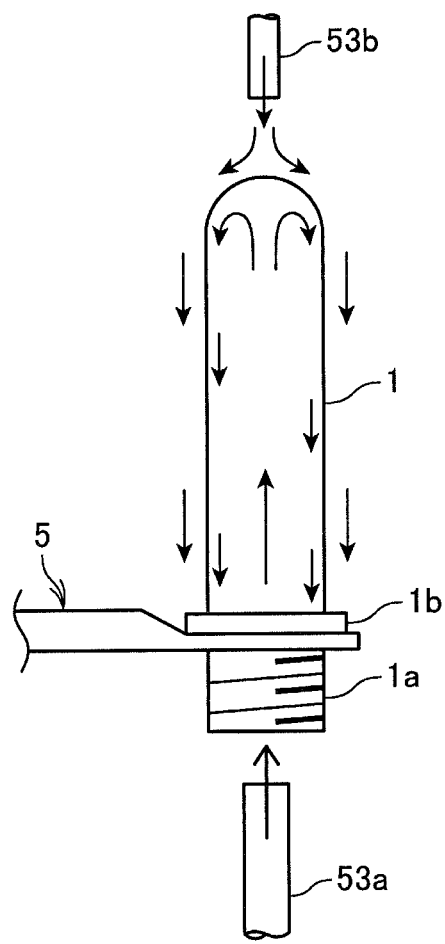
FIG. 4 shows a step of blasting a sterilizer in liquid form to the preform according to the embodiment of the present invention.

Contact of a sterilizer with the preform 1 according to the embodiment of the present invention refers to blasting a gas or mist of a sterilizer or a mixture thereof to the preform 1 as shown in FIG. 3, or blasting a sterilizer in liquid form to the preform 1 which is brought into an inverted position as shown in FIG. 4.

It is preferable that a sterilizer blasted to the preform 1 in the form of a gas, mist or a mixture of a gas and mist contain at least hydrogen peroxide. It is appropriate to set the content of hydrogen peroxide to 0.5% by mass to 65% by mass. When the content of hydrogen peroxide is less than 0.5% by mass, sterilizing power may not be sufficient. On the other hand, when the content of hydrogen peroxide exceeds 65% by mass, it becomes difficult to handle a sterilizer in terms of safety. It is more preferable to set the content of hydrogen peroxide to 0.5% by mass to 40% by mass. When the content of hydrogen peroxide is 40% by mass or less, a sterilizer can be handled more easily, and the concentration of hydrogen peroxide is low and hence, it is possible to reduce the remaining amount of sterilizer after sterilization is performed. A sterilizer contains water. The sterilizer may also contain one, two or more kinds selected from alcohols, such as methyl alcohol, ethyl alcohol, isopropyl alcohol, n-propyl alcohol, and butyl alcohol, ketones, such as acetone, methyl ethyl ketone, and acetylacetone, glycol ether and the like. The sterilizer may further contain organic acid, such as peracetic acid or acetic acid, inorganic acid, such as nitric acid, a basic compound, such as sodium hydroxide or potassium hydroxide, a compound having a sterilization effect, such as sodium hypochlorite, chlorine dioxide or ozone, or an additive, such as a cationic surfactant, a nonionic surfactant, or a phosphoric acid compound.

Figure 5:
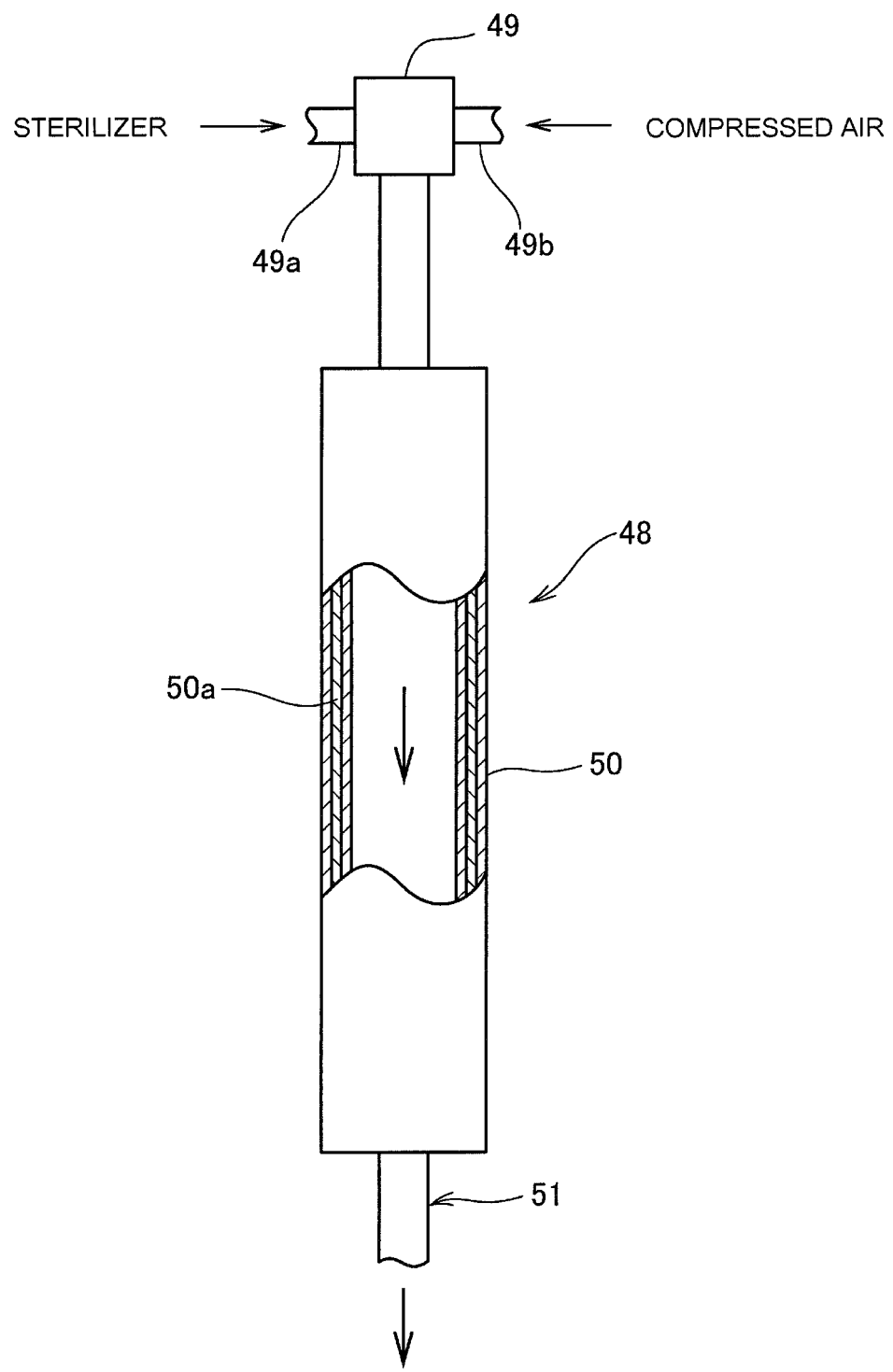
FIG. 5 shows a sterilizer gas generator according to the embodiment of the present invention.

A gas or mist of a sterilizer or a mixture thereof blasted to the preform 1 can be acquired by a sterilizer gas generator 48 shown in FIG. 5. The sterilizer generator 48 includes a sterilizer supply unit 49 and a vaporizing unit 50. The sterilizer gas generator 48 includes a sterilizer supply unit 49 and a vaporizing unit 50. The sterilizer supply unit 49 is formed of a twin-fluid spray nozzle which supplies a sterilizer in the form of a droplet. The vaporizing unit 50 heats the sterilizer supplied from the sterilizer supply unit 49 to a decomposition temperature or below so as to vaporize the sterilizer. The sterilizer supply unit 49 introduces a sterilizer and compressed air respectively from a sterilizer supply path 49a and a compressed air supply path 49b, and sprays the sterilizer into the vaporizing unit 50. The vaporizing unit 50 is formed of a pipe where a heater 50a is sandwiched between the inner and outer walls of the pipe. The vaporizing unit 50 heats a sterilizer sprayed into the pipe so as to vaporize the sterilizer. A gas of the vaporized sterilizer is ejected to the outside of the vaporizing unit 50 from a sterilizer gas blasting nozzle 51. The vaporizing unit 50 may be heated by dielectric heating in place of the heater 50a.

With regard to operation conditions of the sterilizer supply unit 49, for example, the pressure of compressed air is adjusted within a range from 0.05 MPa to 0.6 MPa. When the pressure of compressed air is adjusted within such a range, it is appropriate to set the supply amount of compressed air to 50 L/min. to 300 L/min. Further, a sterilizer may fall under gravity or with a pressure applied. The supply amount of sterilizer may be set as desired. For example, a sterilizer is supplied to the sterilizer supply path 49a within a range from 1 g/min. to 100 g/min. Further, heating the inner surface of the vaporizing unit 50 to between 120° C. and 450° C. causes the sprayed sterilizer to be vaporized.

A gas of a sterilizer is blasted to the preform 1 from the sterilizer gas blasting nozzle 51 as shown in FIG. 3. A gas of a sterilizer flows while being divided into two streams in the sterilizer gas blasting nozzle 51. The gas of the sterilizer is blasted toward the inside of the preform 1 from one nozzle 51a, and the gas of the sterilizer is blasted toward the outer surface of the preform 1 from another nozzle 51b. After the gas of the sterilizer is discharged from the sterilizer gas blasting nozzle 51, the gas of the sterilizer flows into the preform 1 or comes into contact with the outer surface of the preform 1 remaining in the form of a gas, mist, or a mixture of gas and mist.

After the gas or mist of a sterilizer or a mixture thereof blasted toward the inside of the preform 1 flows into the preform 1, the sterilizer flows out from the mouth portion 1a of the preform 1. The flow of the gas or the like of the sterilizer which flows out from the mouth portion 1a impinges on an umbrella-shaped member 52 and is guided by the inner surface of the umbrella-shaped member 52. Accordingly, the flow changes the direction toward the outer surface of the preform 1 so that the flow comes into contact with the outer surface of the preform 1. Forming an annular groove 52a on the umbrella-shaped member 52 causes the gas or the like of the sterilizer flowing out from the mouth portion 1a to flow along the outer surface of the preform 1.

The blast amount of a gas or mist of a sterilizer or a mixture thereof is arbitrarily determined. The blast amount is determined according to the amount of sterilizer supplied to the sterilizer gas generator 48 and a blasting time. A plurality of sterilizer gas generators 48 may be provided. The blast amount varies also depending on the size of the preform 1. A gas or mist of a sterilizer or a mixture thereof ejected from the sterilizer gas blasting nozzle 51 may be blasted to the preform 1 in the state of being diluted with hot air.

In the case where hydrogen peroxide solution is used as a sterilizer, the blast amount of a gas or the like of hydrogen peroxide solution is as follows. The amount of hydrogen peroxide adhering to the preform 1 by blasting a gas or the like of hydrogen peroxide solution to the preform 1 from the sterilizer gas blasting nozzle 51 is preferably set to 0.0035 $\mu L/cm^2$ to 0.35 $\mu L/cm^2$ with respect to the amount of hydrogen peroxide solution which contains 35% by mass of hydrogen peroxide. Further, the concentration of hydrogen peroxide in a gas or the like of hydrogen peroxide solution blasted to the preform 1 is preferably set to 2 mg/L to 20 mg/L, and more preferably set to 5 mg/L to 10 mg/L.

It is preferable that the preform 1 to which a gas or mist of a sterilizer or a mixture thereof be blasted be rinsed with aseptic air. A nozzle which blasts air to the preform 1 may be provided so as to oppose the mouth portion 1a of the preform 1. Alternatively, it is also possible to adopt a configuration where the nozzle which follows at the same speed as the conveyance of the preform 1 is inserted into the preform 1. By performing air rinsing, it is possible to obtain an advantageous effect of activating a sterilizer blasted to the preform 1, and an advantageous effect of removing the sterilizer blasted to the inner surface of the preform 1 and foreign substances and dust which are present on the inner surface. Air used for air rinsing may be at a room temperature or may be heated. However, performing air rinsing with heated air is more advantageous in activating a sterilizer. Rinsing with aseptic air may be performed with the preform 1 being brought into an upright position or an inverted position. Performing rinsing with the preform 1 being brought into an inverted position is more advantageous in removing foreign substances. Further, to remove foreign substances, it is preferable to perform suction in the vicinity of the mouth portion 1a of the preform 1 which is brought into an inverted position. The amount of air blasted is preferably set to 0.04 L/preform to 400 L/preform. In the case where hydrogen peroxide solution is used as a sterilizer, it is preferable to set the amount of hydrogen peroxide adhering to the preform 1 which is rinsed with aseptic air to a range from 0.0003 $\mu L/cm^2$ to 0.35 $\mu L/cm^2$ in terms of hydrogen peroxide solution containing 35% by mass of hydrogen peroxide. It is more preferable to set the amount to 0.0004 $\mu L/cm^2$ to 0.2 $\mu L/cm^2$. By setting this adhesion amount of hydrogen peroxide to 0.0003 $\mu L/cm^2$ or more, it is possible to obtain sufficient sterilization effect. Further, in the case where the adhesion amount of hydrogen peroxide exceeds 0.35 $\mu L/cm^2$, when blow molding is performed, defective molding, such as whitening, spot, wrinkles, or deformation is generated on the container 2.

In a sterilization method where a gas or mist of a sterilizer or a mixture thereof is blasted to the preform 1, a gas or mist of a sterilizer or a mixture thereof is generated in a blasting step and an air rinsing step which follows the blasting step and hence, it is necessary to evacuate the inside of the preform sterilizing unit chamber 8. Discharged air is made harmless by a processing device, and is then released.

A sterilizer in liquid form is blasted to the preform 1 which is brought into an inverted position as shown in FIG. 4. To cause a sterilizer in liquid form to come into contact with the entire inner surface of the preform 1, the sterilizer in liquid form is blasted to the inner surface of the preform 1 from the mouth portion 1a by a sterilizer blasting nozzle 53a which is pointing upward in a state where the support ring 1b of the preform 1 in an inverted position is held by the gripper 5. Further, a sterilizer in liquid form is blasted to the outer surface of the preform 1 by a sterilizer blasting nozzle 53b which is pointing downward such that the sterilizer in liquid form comes into contact with the entire outer surface of the preform 1. The sterilizer blasting nozzle 53a may be provided so as to oppose the mouth portion 1a of the preform 1. Alternatively, it is also possible to adopt a configuration where the nozzle 53a which follows at the same speed as the conveyance of the preform 1 is provided, and the nozzle 53a is inserted into the preform 1. The number of sterilizer blasting nozzles 53b may be a plural. Further, provided that a sterilizer in liquid form is allowed to come into contact with the inner and outer surfaces of the preform 1, a method is not limited to that a sterilizer in liquid form is blasted by a nozzle. It is also possible to adopt a method where the preform 1 is immersed in a sterilizer in liquid form.

It is preferable that a sterilizer in liquid form contain peracetic acid. It is also preferable that a sterilizer in liquid form be equilibrium peroxide composition made of peracetic acid, hydrogen peroxide, acetic acid and water. The concentration of peracetic acid is preferably set to 500 mg/L to 4000 mg/L. When the concentration of peracetic acid is less than 500 mg/L, sterilizing power is insufficient. On the other hand, when the concentration of peracetic acid exceeds 4,000 mg/L, the concentration of peracetic acid is high and hence, a member, such as a packing, used in the aseptic filling apparatus may be deteriorated. A sterilizer containing sterilization component, such as hydrogen peroxide, sodium hypochlorite, chlorine dioxide, or ozone, may be used as a sterilizer in liquid form. A sterilizer in liquid form contains water. However, a sterilizer may contain one kind or two or more kinds selected from alcohols, such as methyl alcohol, ethyl alcohol, isopropyl alcohol, n-propyl alcohol, or butyl alcohol, ketones, such as acetone, methyl ethyl ketone, or acetylacetone, glycol ethers and the like. A sterilizer may further contain inorganic acid, such as nitric acid, basic compound, such as sodium hydroxide or potassium hydroxide, or an additive, such as a cationic surfactant, a nonionic surfactant, or a phosphoric acid compound.

A sterilizer in liquid form is heated to 50° C. to 80° C., and preferably to 60° C. to 70° C. Heating a sterilizer increases sterilization effect of the sterilizer. It is preferable to set the flow rate in one sterilizer blasting nozzle 53a, 53b to 1 L/min. to 15 L/min., and it is appropriate to set the flow rate to 3 L/min. to 10 L/min. Further, it is appropriate to set a blasting time to 0.2 seconds to 5 seconds. The blast amount of sterilizer in liquid form to the preform 1 is determined according to the flow rate and the blasting time of the sterilizer blasting nozzles 53a and 53b. It is preferable to set the blast amount to 0.05 ml/cm² to 20 ml/cm² with respect to the surface area of the preform 1. When the blast amount is less than 0.05 ml/cm², sterilization is not sufficiently performed. On the other hand, when the blast amount exceeds 20 ml/cm², sterilization is excessively performed, thus leading to waste of energy and a sterilizer.

The preform 1 with which a sterilizer in liquid form is caused to come into contact is rinsed with aseptic water so as to remove sterilizer adhering to the preform 1. Aseptic water is produced by heating water for 4 minutes or more at 121° C. or above, or by causing water to pass through an aseptic filter. The preform 1 is rinsed with aseptic water by steps and devices substantially equal to steps and devices used for blasting a sterilizer shown in FIG. 4. To cause the entire inner surface of the preform 1 to be rinsed with aseptic water, aseptic water is blasted to the inner surface of the preform 1 from the mouth portion 1a by a nozzle which is pointing upward in a state where the support ring 1b of the preform 1 in an inverted position is held by the gripper 5. Further, to cause the entire outer surface of the preform 1 to be rinsed with aseptic water, aseptic water is blasted to the outer surface of the preform by a nozzle which is pointing downward. The nozzle which is pointing upward may be provided so as to oppose the mouth portion 1a of the preform 1. Alternatively, it is also possible to adopt a configuration where a nozzle which follows at the same speed as the conveyance of the preform 1 is provided, and the nozzle is inserted into the preform 1. Further, the number of nozzles which point downward may be a plural.

Aseptic water is adjusted to 10° C. to 80° C., and preferably to 30° C. to 70° C. It is preferable to set the flow rate in one nozzle which blasts aseptic water to 1 L/min. to 15 L/min., and it is appropriate to set the flow rate to 3 L/min. to 10 L/min. Further, it is appropriate to set a blasting time to 0.1 seconds to 15 seconds. The blast amount of aseptic water to the preform 1 is determined according to the flow rate and the blasting time of the nozzle. It is preferable to set the blast amount to 0.05 ml/cm² to 20 ml/cm² with respect to the surface area of the preform 1. When the blast amount is less than 0.05 ml/cm², rinsing is not sufficiently performed. On the other hand, when the blast amount exceeds 20 ml/cm², sterilization is excessively performed, thus leading to waste of energy.

Container sterilization is performed on the container 2 acquired by performing blow molding on the sterilized preform 1. Accordingly, to remove a sterilizer adhering to the preform 1, water (pure water or the like) which is compatible with beverages may be used instead of aseptic water. It is also possible to adopt a configuration where air which is made to pass through a filter for removing foreign substances and dust is blasted to the preform 1 so as to remove a sterilizer adhering to the preform 1 instead of rinsing the preform 1 with water. However, in the case where a substance other than aseptic water and aseptic air is used, there is a possibility that the preform 1 is contaminated with bacteria and the like. Such contamination is included in sterilizing ability X [LRV] in the preform sterilization step.

It is preferable that aseptic water adhering to the preform 1 which is rinsed with aseptic water be removed by blasting aseptic air to the inner and outer surfaces of the preform 1. The reason is as follows. The preform 1 is heated to a molding temperature in the heating unit 12. In such a case, there is a possibility that non-uniform heating is generated at a portion of the preform 1 to which aseptic water adheres so that defective molding, such as whitening or uneven thickness, is generated on the molded container 2.

Figure 6:
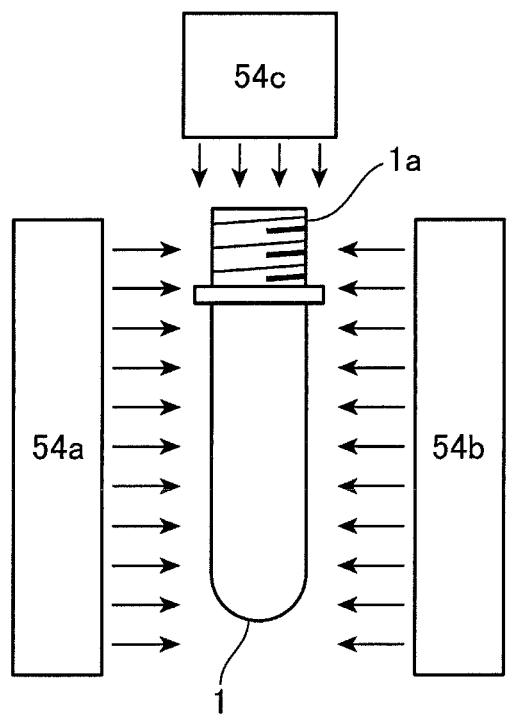
FIG. 6 shows a step of irradiating the preform with electron beam according to the embodiment of the present invention.

Irradiation with electron beam to the preform 1 according to the embodiment of the present invention refers to irradiating the inner and outer surfaces of the conveyed preform 1 with electron beam by electron beam irradiation devices 54a, 54b and 54c as shown in FIG. 6. Electron beam has a sterilization effect so that bacteria and the like adhering to the surface of the preform 1 are sterilized by irradiation with electron beam. In FIG. 6, the preform 1 is irradiated with electron beam from three directions. However, any method may be adopted provided that the inner and outer surfaces of the preform 1 are irradiated with electron beam. For example, if the preform 1 is rotated, the electron beam irradiation device 54b becomes unnecessary. It is also possible to adopt a configuration where a reflection mirror is provided at a position above the mouth portion 1a of the preform 1, and electron beam emitted from the electron beam irradiation device 54a is introduced into the preform 1 from the mouth portion 1a of the preform 1. It is also possible to adopt a configuration where a rod-shaped electron beam irradiation device is inserted into the preform 1, and the inner surface of the preform 1 is irradiated with electron beam.

The electron beam irradiation devices 54a, 54b, 54c may have any structure. For example, there are a scanning-type electron beam irradiation device and a monofilament-type electron beam irradiation device. An electron beam irradiation device of a low output type having an output of 100 kV to 500 kV is preferable in terms of ease of handling.

It is preferable that foreign substances adhering to the inner and outer surfaces of the preform 1 be removed before the preform 1 is irradiated with electron beam. The reason is as follows. In the case where foreign substances adhere to the surface of the preform 1, such portions are not irradiated with electron beam and hence, there is a possibility that sterilization is poorly performed. To remove foreign substances from the preform 1, air is blasted or water is blasted with the preform 1 being brought into an upright position or an inverted position. In the case where water is blasted, it is also necessary to remove such water and hence, it is preferable to blast air. It is preferable that ionized air be blasted to the preform 1 before air is blasted, thus eliminating static electricity. It is also preferable that a suction nozzle be provided at a position in the vicinity of the mouth portion 1a of the preform 1 so as to suck foreign substances and to remove the foreign substances to the outside of the aseptic filling apparatus. The step of removing foreign substances on the preform 1 is performed on the preform supply conveyor 4 disposed outside the preform sterilizing unit chamber 8. After the foreign substances are removed, the preform 1 is conveyed into the preform sterilizing unit chamber 8. In the case where a function of removing bacteria and the like is recognized with a function of removing foreign substances, such a function is also included in sterilizing ability X [LRV] in the preform sterilization step.

Electron beam changes oxygen into ozone. Accordingly, ozone is generated if oxygen is present in the atmosphere where irradiation with electron beam is performed. To remove generated ozone, it is necessary to evacuate the inside of the preform sterilizing unit chamber 8. When the atmosphere where irradiation with electron beam is performed is replaced by nitrogen or the like, it is possible to suppress the generation of ozone.

Figure 7:
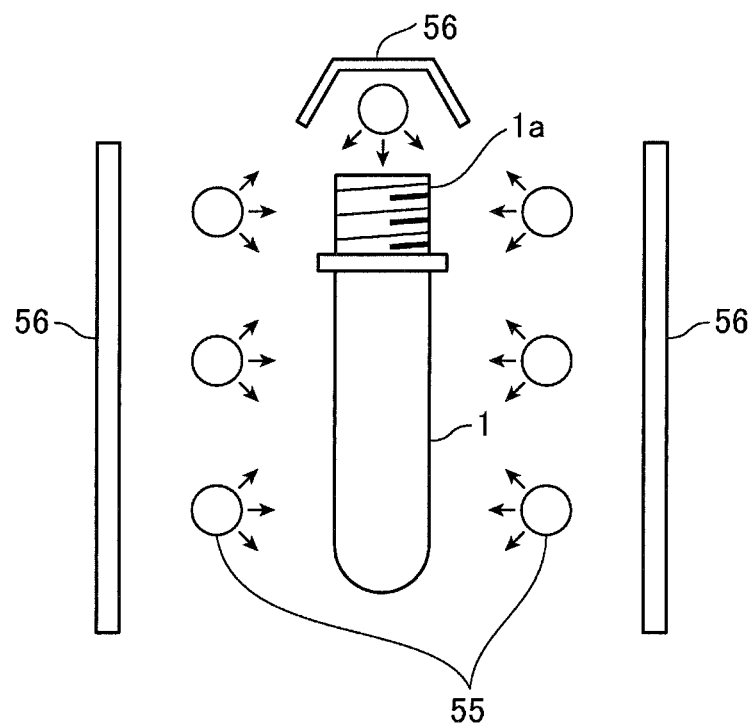
FIG. 7 shows a step of irradiating the preform with light containing ultraviolet rays according to the embodiment of the present invention.

Irradiation with light containing ultraviolet rays to the preform 1 according to the embodiment of the present invention refers to irradiating the inner and outer surfaces of the preform 1 with light containing ultraviolet rays emitted from light irradiation lamps 55 as shown in FIG. 7. On the side of the light irradiation lamps 55 opposite to the preform 1, it is preferable to provide light reflecting plates 56, which reflect emitted light, and cause the light to be directed to the preform 1.

Ultraviolet ray contained in emitted light is one kind of an electromagnetic wave having wavelength of 100 nm to 380 nm. Emitted light has any of these wavelengths. A wavelength of 100 nm to 280 nm referred to as UV-C is particularly effective for sterilization. Further, a wavelength of 253.7 nm has the greatest sterilization effect so that it is optimum to have a wavelength of 253.7 nm.

The light irradiation lamp 55 which emits ultraviolet rays having 100 nm to 380 nm may be a low pressure mercury lamp, a high pressure mercury lamp, a xenon flash lamp or the like. Particularly, light (wavelength: 100 to 950 nm) emitted from a xenon flash lamp into which a xenon gas is sealed in the lamp has high sterilization effect. Accordingly, it is optimum that the light irradiation lamp 55 is formed of a xenon flash lamp.

A sterilization effect brought about by irradiation with light containing ultraviolet rays is proportional to the amount of light irradiation per unit area and an irradiation time. However, light from a xenon flash lamp has higher sterilization effect than light emitted from a low pressure mercury lamp or a high pressure mercury lamp and hence, sterilization can be sufficiently performed by performing irradiation for a short time. Accordingly, it is possible to avoid an increase in temperature of the mouth portion of the preform 1 caused by light irradiation.

The number of light irradiation lamps 55 is not limited provided that the entire inner and outer surfaces of the preform 1 are irradiated. As shown in FIG. 7, a large number of light irradiation lamps 55 may be provided so as to irradiate the outer surface and the inner surface with light containing ultraviolet rays. However, if the preform 1 is rotated, the light irradiation lamps 55 which irradiate the side surface of the preform 1 may be arranged in one row. To irradiate the inner surface of the preform 1 with light containing ultraviolet rays, it is preferable that the light irradiation lamp 55 be provided so as to oppose the mouth portion 1*a* of the preform 1, and the inner surface of the preform 1 is irradiated with light containing ultraviolet rays through the opening portion of the mouth portion 1*a*. It is also preferable that the light reflecting plate 56 be provided so as to have a dome shape toward the mouth portion 1*a*, and the inner surface of the preform 1 is efficiently irradiated with light emitted from the light irradiation lamp 55 and containing ultraviolet rays. To irradiate the inner surface of the preform 1 with light containing ultraviolet rays, it is also possible to adopt a configuration where a rod-shaped light irradiation lamp is inserted into the preform 1, and the inner surface of the preform 1 is irradiated with light containing ultraviolet rays. The light irradiation lamp 55 may have any shape, such as a round shape, a rod shape, or a U shape.

The light reflecting plates 56 shown in FIG. 7 have a purpose of efficiently irradiating the preform 1 with light emitted from the light irradiation lamps 55 and containing ultraviolet rays. Accordingly, the light reflecting plates 56 are provided on the side of the light irradiation lamps 55 opposite to the preform 1. The light reflecting plate 56 may have a flat surface, a curved surface, or a combination of a plurality of surfaces having a flat surface or a curved surface. The light reflecting plate 56 may have any structure provided that the light reflecting plate 56 can reflect light containing ultraviolet rays. For example, the light reflecting plate 56 may be a light reflecting plate which is made of a synthetic resin, metal, or glass, and which has the smooth surface. The light reflecting plate 56 may be a light reflecting plate on which coating, metal plating, or vapor deposition of metal, metal oxide or the like is performed so as to make the surface smoother. The light reflecting plate 56 may also be a light reflecting plate which is obtained by combining the above-mentioned configurations.

It is preferable that foreign substances adhering to the inner and outer surfaces of the preform 1 be removed before the preform 1 is irradiated with light containing ultraviolet rays. The reason is as follows. In the case where foreign substances are adhering to the surface of the preform 1, such portions are not irradiated with light containing ultraviolet rays and hence, there is a possibility that sterilization is poorly performed. To remove foreign substances from the preform 1, air is blasted or water is blasted with the preform 1 being brought into an upright position or an inverted position. In the case where water is blasted, it is necessary to remove such water and hence, it is preferable to blast air. It is preferable that ionized air be blasted to the preform 1 before air is blasted, thus eliminating static electricity. It is also preferable that a suction nozzle be provided at a position in the vicinity of the mouth portion 1*a* of the preform 1 so as to suck foreign substances and to remove the foreign substances to the outside of the aseptic filling apparatus. The step of removing foreign substances on the preform 1 is performed on the preform supply conveyor 4 disposed outside the preform sterilizing unit chamber 8. After the foreign substances are removed, the preform 1 is conveyed into the preform sterilizing unit chamber 8.

Light containing ultraviolet rays changes oxygen into ozone. Accordingly, ozone is generated if oxygen is present in the atmosphere where irradiation with light containing ultraviolet rays is performed. To remove generated ozone, it is necessary to evacuate the inside of the preform sterilizing unit chamber 8. When the atmosphere where irradiation with light containing ultraviolet rays is performed is replaced by nitrogen or the like, it is possible to suppress the generation of ozone.

Contact of hot water with the preform 1 according to the embodiment of the present invention is performed by blasting hot water to the inner and outer surfaces of the preform 1 by a nozzle in the same manner as the step of blasting a sterilizer in liquid form to the preform 1 which is brought into an inverted position shown in FIG. 4. Bacteria and the like adhering to the surface of the preform 1 are sterilized by heat of hot water. To cause the entire inner surface of the preform 1 to be sterilized with hot water, hot water is blasted to the inner surface of the preform 1 from the mouth portion 1*a* by a nozzle which is pointing upward in a state where the support ring 1*b* of the preform 1 in an inverted position is held by the gripper 5. Further, to cause the entire outer surface of the preform 1 to be sterilized with hot water, hot water is blasted to the outer surface of the preform 1 by a nozzle which is pointing downward. The nozzle which is pointing upward may be provided so as to oppose the mouth portion 1*a* of the preform 1. Alternatively, it is also possible to adopt a configuration where a nozzle which follows at the same speed as the conveyance of the preform 1 is provided, and the nozzle is inserted into the preform 1. Further, the number of nozzles which point downward may be a plural.

Hot water refers to water or aseptic water heated to 70° C. to 100° C. It is preferable to set the flow rate in one nozzle which blasts hot water to 1 L/min. to 15 L/min., and it is appropriate to set the flow rate to 3 L/min. to 10 L/min. Further, it is appropriate to set a blasting time to 0.1 seconds to 15 seconds. The blast amount of hot water to the preform 1 is determined according to the flow rate and the blasting time of the nozzle. It is preferable to set the blast amount to 0.05 ml/cm$^2$ to 20 ml/cm$^2$ with respect to the surface area of the preform 1. When the blast amount is less than 0.05 ml/cm$^2$, sterilization is not sufficiently performed. On the other hand, when the blast amount exceeds 20 ml/cm$^2$, sterilization is excessively performed, thus leading to waste of energy.

It is preferable that hot water adhering to the preform 1 which is sterilized with hot water be removed by blasting aseptic air to the inner and outer surfaces of the preform 1. The reason is as follows. The preform 1 is heated to a molding temperature in the heating unit 12. In such a case, there is a possibility that non-uniform heating is generated at a portion of the preform 1 to which hot water adheres so that defective molding, such as whitening or uneven thickness, is generated on a molded container. Air blasted to the preform 1 may be aseptic air which is made to pass through an aseptic filter.

Figure 8:
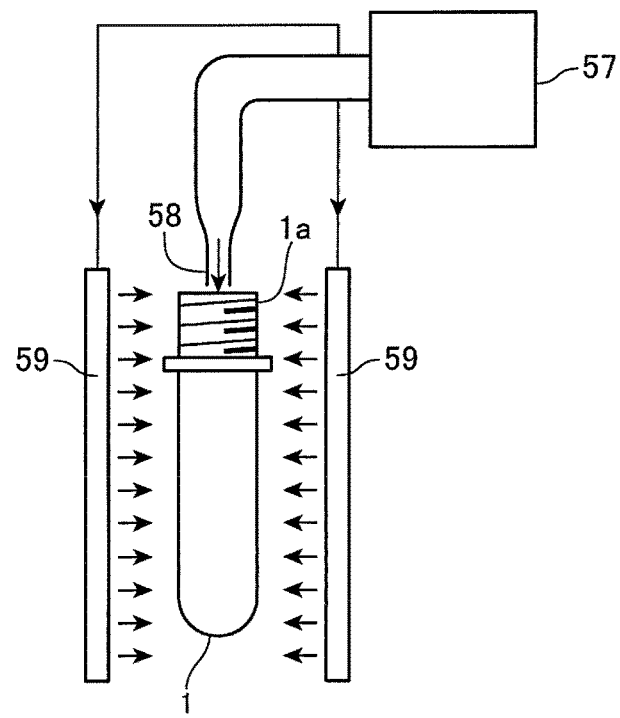
FIG. 8 shows a step of blasting superheated steam to the preform according to the embodiment of the present invention.

Contact of superheated steam with the preform 1 according to the embodiment of the present invention refers to, as shown in FIG. 8, blasting superheated steam generated from a superheated steam generation device 57 to the inner and outer surfaces of the preform 1 from a superheated steam blasting nozzle 58 and superheated steam blasting slits 59. Bacteria and the like adhering to the surface of the preform 1 are sterilized by heat of superheated steam.

Superheated steam is steam which is generated from water supplied to the superheated steam generation device 57, and which has a pressure of 0.1 MPa to 0.3 MPa higher than an atmospheric pressure with 200° C. to 500° C. The superheated steam generation device 57 heats a water passing pipe by a heater or an induction coil, thus generating superheated steam. The generated superheated steam is ejected from the superheated steam blasting nozzle 58, and is blasted to the inner surface of the preform 1. Further, superheated steam generated in the superheated steam generation device 57 is introduced into the superheated steam blasting slits 59, and the superheated steam is blasted to the outer surface of the preform 1.

A compound having sterilization effect, such as hydrogen peroxide, may be added to water supplied to the superheated steam generation device 57. For example, adding 5% by mass of hydrogen peroxide to water enhances a sterilization effect.

By rotating the preform 1, superheated steam can be efficiently blasted to the outer surface. Further, it is also possible to adopt a configuration where the superheated steam blasting nozzle 58 is inserted into the preform 1 so as to blast superheated steam to the inner surface of the preform 1. Sterilization can be performed with blast of a short time and hence, there is no possibility that the mouth portion 1$a$ is deformed, and a resin for forming the preform 1 is excessively heated. There is also no possibility that drain of steam remains in the preform 1. Accordingly, it is possible to convey the preform 1 to the heating unit 12 without removing drain.

As described above, the preform 1 is, in the preform sterilizing unit 6, sterilized by any one, two or more methods selected from contact with a sterilizer, irradiation with electron beam, irradiation with light containing ultraviolet rays, contact with hot water, and contact with superheated steam. Sterilizing ability in the sterilization step performed in the preform sterilizing unit 6 is expressed by X [LRV]. Sterilizing ability 1 [LRV] refers to sterilizing ability to reduce the number of viable cells to ¹⁄₁₀. X [LRV] refers to ability to reduce the number of viable cells to $1/10^X$.

Sterilizing ability of the preform sterilizing unit 6 is calculated such that indicator bacteria are caused to adhere to the preform 1 and sterilization is performed and, thereafter, presence or absence of mortality of indicator bacteria is checked. For example, 1 g of indicator bacteria with $10^4$ [cfu/g] is caused to adhere to the inner surface of the preform 1, the preform 1 is sterilized, the sterilized preform 1 is filled with a culture medium so as to culture. When the propagation of bacteria is not observed, sterilizing ability of the preform sterilizing unit 6 is 4 or more. By performing sterilization under conditions where various numbers of indicator bacteria are caused to adhere to the preform 1, sterilizing ability of the preform sterilizing unit 6 can be determined.

Figure 9:
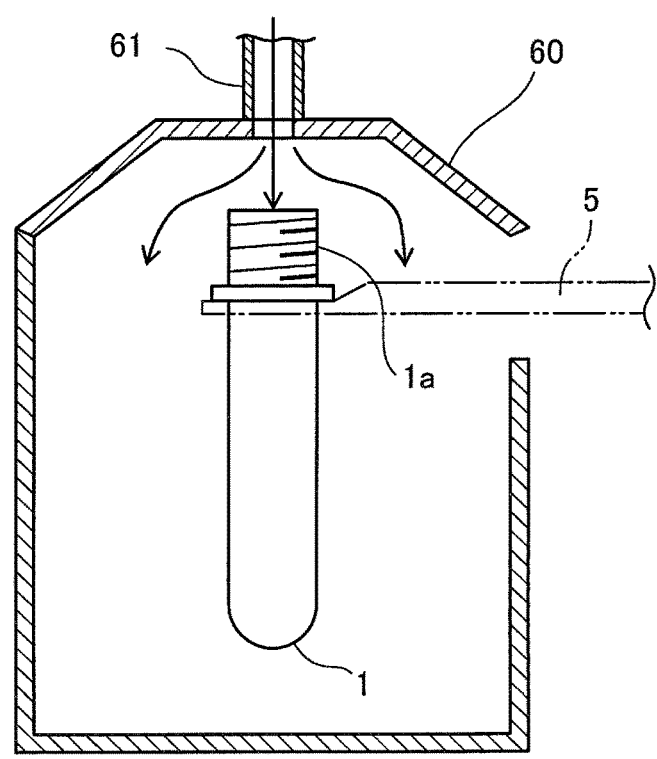
FIG. 9 shows a step of supplying aseptic air to the preform according to the embodiment of the present invention.

The preform 1 sterilized in the preform sterilizing unit 6 is conveyed to a heating unit conveyance wheel 10 through a wheel 9 in a state where the support ring 1$b$ of the preform 1 is held. As shown in FIG. 9, a preform tunnel 60 may be provided to the preform 1 in the wheel 9 and the heating unit conveyance wheel 10 such that the preform tunnel 60 encloses a conveying path for the preform 1. The preform tunnel 60 covers the mouth portion 1$a$ of the preform 1 from above, and the ceiling portion of the preform tunnel 60 is formed into a roof shape having inclined surfaces. Further, a preform aseptic air supply nozzle 61 is provided to the ceiling portion in the form of pipes arranged in a row or in the form of a slit. The preform aseptic air supply nozzle 61 blows out aseptic air toward the mouth portion 1$a$ of the preform 1. With such a configuration, aseptic air is efficiently supplied to the preform 1 so that the preform 1 can travel in the molding unit chamber 18 while asepticity is maintained. Aseptic air is obtained by causing air from a blower to pass through an aseptic filter. Alternatively, aseptic air may be obtained such that compressed air with a high propulsive force is brought into an aseptic state by an aseptic filter.

Figure 10:
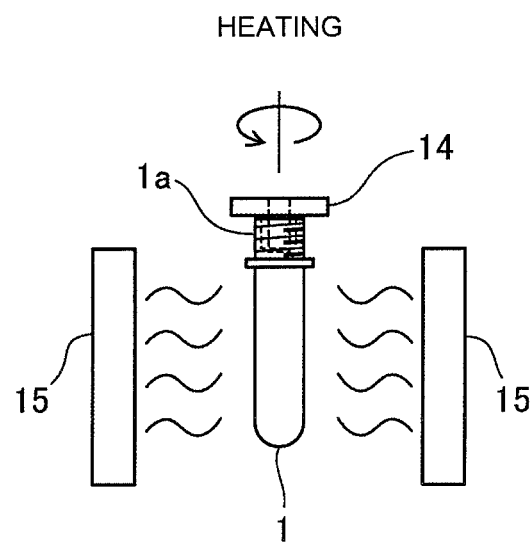
FIG. 10 shows a step of heating the preform according to the embodiment of the present invention.

The preform 1 conveyed to the heating unit conveyance wheel 10 is released from the gripper 5 as shown in FIG. 10. A spindle 14 is inserted into the mouth portion 1$a$ of the preform 1, and the preform 1 is conveyed to the heating unit 12. As shown in FIG. 10, the preform 1 which enters the heating unit 12 is heated, by an infrared heater 15 or another heating device, to a temperature suitable for blow molding which is performed thereafter. It is preferable to set such a temperature to 90° C. to 130° C. The temperature of the mouth portion 1$a$ of the preform 1 is suppressed to 70° C. or below so as to prevent deformation or the like.

To increase sterilization effect on the mouth portion 1$a$ and the support ring 1$b$ of the preform 1, the infrared heater 15 which heats only the mouth portion 1$a$ and the support ring 1$b$ may be provided. By providing the infrared heater 15 which heats only the mouth portion 1$a$ and the support ring 1$b$ in a separated manner from the infrared heater 15 which heats a barrel portion, the heating temperature of the mouth portion 1$a$ and the support ring 1$b$ can be controlled. By controlling the temperature of the mouth portion 1$a$ and the support ring 1$b$ to 40° C. to 70° C., preferably to 45° C. to 65° C., a sterilizer, such as hydrogen peroxide, adsorbed to the inner and outer surfaces of the mouth portion 1$a$ and the support ring 1$b$ is activated, thus enhancing a sterilization effect. It is also possible to reduce the amount of the remaining sterilizer component. It is possible to adopt a configuration where, to cool the mouth portion 1$a$ and the support ring 1$b$ before blow molding is performed on the preform 1, aseptic air is blasted to the mouth portion 1$a$ and the support ring 1$b$ in a wheel 16.

As shown in FIG. 10, the preform 1 is conveyed in the heating unit 12 in a state where the spindle 14 is inserted into the mouth portion 1a, and the preform 1 is rotated. The spindles 14 are provided to an endless chain 13 at fixed intervals. The endless chain 13 is rotated by a pulley 11. The preform 1 may be conveyed such that a mandrel is inserted into the preform 1 in place of the spindle 14, and the preform 1 is conveyed while being rotated in an inverted position.

The heated preform 1 is released from the spindle 14, and is conveyed to a mold wheel 19 of the molding unit 17 through the wheel 16 in a state where the heated preform 1 is held by the gripper 5. In the same manner as the wheel 9 and the heating unit conveyance wheel 10, the wheel 16 may adopt a configuration where the preform tunnel 60 as shown in FIG. 9 is provided so as to enclose a conveying path for the preforms 1, and aseptic air is blasted to the preform 1.

The heated preform 1 is passed to the mold wheel 19 from the wheel 16. The preform 1 passed to the mold wheel 19 is blow molded into the container 2 as shown in FIG. 11 by a die 20 provided to the mold wheel 19. The plurality of dies 20 and a plurality of blow nozzles 21 are arranged around the mold wheel 19, and turns around the mold wheel 19 at a fixed speed with the rotation of the mold wheel 19. When the heated preform 1 arrives, the die 20 sandwiches the preform 1. Subsequently, the blow nozzle 21 is joined to the preform 1, an extendable rod 22 is introduced into the preform 1 while being guided by a hole formed in the blow nozzle 21, and a gas with high pressure, such as air, is blown into the preform 1 from the blow nozzle 21. With such operations, the container 2 is molded in the die 20. The molded container 2 is taken out from the die 20, and is passed to the inspection wheel 23 in a state where the support ring 1b is held by a gripper 22 provided to an inspection wheel 23.

Figure 12:
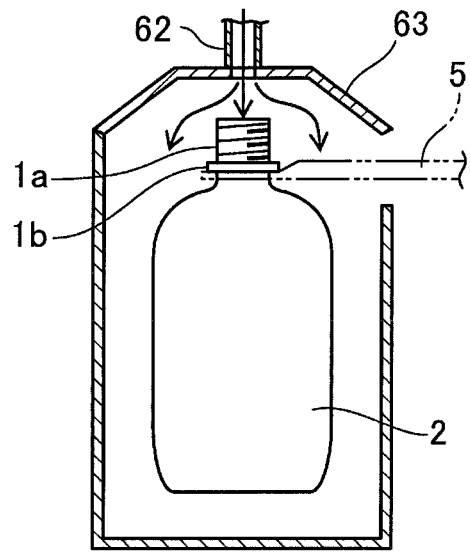
FIG. 12 shows a step of supplying aseptic air to a container according to the embodiment of the present invention.

The molded container 2 is inspected by the inspection device 24 provided to the inspection wheel 23. As shown in FIG. 12, a container tunnel 63 may be provided to extend to the inspection device 24 such that the container tunnel 63 encloses a conveying path for the containers 2. The container tunnel 63 covers the mouth portion 1a of the container 2 from above, and a ceiling portion is formed into a roof shape having inclined surfaces. Further, a container aseptic air supply nozzle 62 is provided to the ceiling portion in the form of pipes arranged in a row or in the form of a slit. The container aseptic air supply nozzle 62 blows out aseptic air toward the mouth portion 1a of the container 2. With such a configuration, aseptic air is efficiently supplied to the container 2, and the container 2 can travel around the inspection wheel 23 while asepticity is maintained. Aseptic air is obtained by causing air from a blower to pass through an aseptic filter. Alternatively, aseptic air may be obtained such that compressed air with a high propulsive force is brought into an aseptic state by an aseptic filter. The container 2 which is inspected is conveyed to the container sterilizing unit 30 through wheels 25 and 26 in the atmosphere shut-off chamber 27. At this point of operation, also in the wheels 25 and 26, the container 2 may be conveyed in a state where the container 2 is enclosed by the container tunnel 63, and aseptic air is supplied to the inside of the container tunnel 63 from the container aseptic air supply nozzle 62. The container 2 is conveyed in the container tunnel 63 so that contamination with bacteria and the like can be suppressed.

The molded container 2 is inspected by the inspection device 24 provided around the inspection wheel 23 with respect to a temperature of the container, the barrel portion of the container, the support ring 1b, the top surface of the mouth portion of the container, the bottom portion of the container and the like. When it is determined that the container 2 is abnormal, the container 2 is discharged to the outside of the aseptic filling apparatus by a discharging device not shown in the drawing.

In the container temperature inspection, the surface temperature of the container 2 is inspected so as to determine the state of the container 2. A temperature sensor is an infrared radiation thermometer, for example. However, it is also possible to use another thermometer. In the case where contact with a sterilizer is adopted as a method for sterilizing the container 2, causing remaining heat at the time of molding a container to remain in the container 2 is necessary to appropriately sterilize the container 2. It is preferable that a temperature detected by a temperature sensor be 40° C. or above. In the case where the container 2 is sterilized by another method, it is not always necessary to measure the temperature of the container 2.

Further, the barrel portion of the container, the support ring 1b, the top surface of the mouth portion of the container, and the bottom portion of the container are imaged by a camera so as to inspect states of the respective portions. The imaged image is processed by an image processing apparatus, and presence or absence of abnormalities, such as flaws, foreign substances, deformations, or discoloring is determined. The container 2 beyond an allowable range is determined as abnormal. The container 2 determined as abnormal is discharged to the outside of the aseptic filling apparatus by a discharging device not shown in the drawing.

The container 2 which is not determined as abnormal in the inspection performed by the inspection device 24 is conveyed to the sterilizing unit 30 through the wheels 25, 26 in the atmosphere shut-off chamber 27 provided between the molding unit 17 and the sterilizing unit 30 so as to prevent a gas or mist of a sterilizer or a mixture thereof or ozone generated in the sterilizing unit 30 from flowing into the molding unit 17. In the case where a method for sterilizing the container 2 is contact with hot water or filling with heated contents where a gas or mist of a sterilizer or a mixture thereof or ozone is not generated, it is not always necessary to provide the atmosphere shut-off chamber 27.

After the preform 1 and the container 2 are discharged from the preform sterilizing unit chamber 8 of the preform sterilizing unit 6 and before the preform 1 and the container 2 are conveyed to the inside of the container sterilizing unit chamber of the container sterilizing unit 30, there is a possibility that the preform 1 and the container 2 are contaminated with bacteria and the like during a period where the preform 1 and the container 2 are conveyed through the heating unit 12, the molding unit 17, the inspection wheel 23, and the atmosphere shut-off chamber 27. It is possible to realize that the devices in the molding unit chamber 18 are completely sterilized, and blow molding is performed on the preform 1 while asepticity is maintained, thus forming the container 2. However, it is necessary to change all members and structural bodies of a general blow-molding machine to members resistant to a sterilizer, and to a structure which can maintain aseptic. Accordingly, such a configuration is not economical. It is possible to perform sterilization such that, before operation of the aseptic filling apparatus is started, a sterilizer containing a component having a sterilization effect, such as hydrogen peroxide, hypochlorous acid, or ozone with a low concentration is gasified and blasted to the inside of the molding unit chamber 18, or the preform 1 is filled with a sterilizer, and the preform 1 is molded into the container 2 by the molding unit 17. However, it is difficult to perform sterilization completely.

Accordingly, there is a possibility that the preform 1 is contaminated with bacteria and the like during a period after the preform 1 is discharged from the preform sterilizing unit chamber 8 of the preform sterilizing unit 6 and before the preform 1 is conveyed into the container sterilizing unit chamber 31 of the container sterilizing unit 30. That is, there is a possibility that the preform 1 and the container 2 are contaminated with bacteria and the like during a period from the heating step and before the container sterilization step. Accordingly, in the container sterilization step, it is necessary to eliminate at least bacteria and the like which contaminate during these steps. Further, in the case where sterilization effect in the preform sterilization step is less than 5 [LRV], it is also necessary to add a sterilization effect which can complement the sterilization effect.

The container 2 conveyed to the container sterilizing unit 30 is passed to a container sterilizing wheel 28 where the large number of grippers 5 are provided at fixed intervals, and the container 2 is sterilized on the container sterilizing wheel 28. The container 2 is sterilized by performing any one, two or more selected from contact with a sterilizer, irradiation with electron beam, irradiation with light containing ultraviolet rays, contact with hot water, and filling of a heated content. Sterilization of the container 2 by filling with heated contents is performed by filling with heated contents in the filling unit 37 without providing the container sterilizing unit 30 and the air rinsing unit 32.

Figure 13:
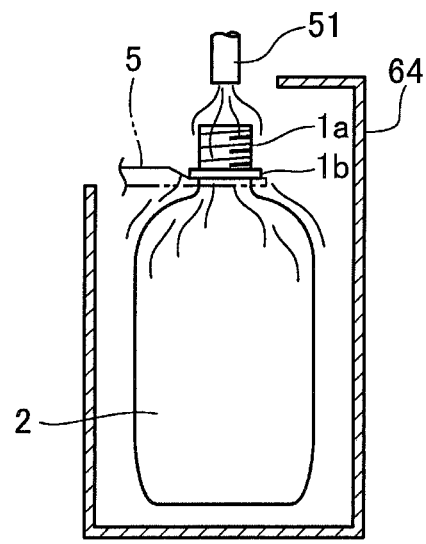
FIG. 13 shows a step of blasting a sterilizer gas to the container according to the embodiment of the present invention.
Figure 14:
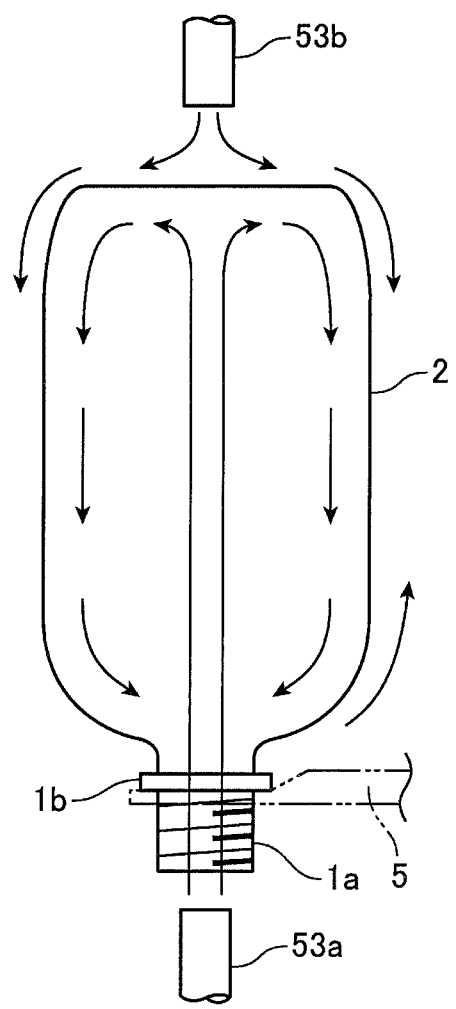
FIG. 14 shows a step of blasting a sterilizer in liquid form to the container according to the embodiment of the present invention.

Contact of sterilizer with the container 2 according to the embodiment of the present invention refers to blasting a gas or mist of a sterilizer or a mixture thereof to the container 2 as shown in FIG. 13, or blasting a sterilizer in liquid form to the container 2 which is brought into an inverted position as shown in FIG. 14. It is preferable that the container 2 with which a sterilizer is caused to come into contact have remaining heat generated at the time of molding the preform 1, and a portion of the remaining heat be 40° C. or above. This is because sterilization effect of a sterilizer is enhanced by the remaining heat which remains in the container 2.

To blast a gas or mist of a sterilizer or a mixture thereof to the container 2, as shown in FIG. 13, the sterilizer gas blasting nozzle 51 is provided. The sterilizer gas blasting nozzle 51 is provided such that a nozzle hole formed at the distal end of the sterilizer gas blasting nozzle 51 can oppose an opening of the mouth portion 1*a* of the container 2 which travels just below the nozzle hole. Further, as shown in FIG. 13, a sterilizer gas blasting tunnel 64 is provided below the sterilizer gas blasting nozzle 51 along the travel path of the container 2, when necessary. The number of sterilizer gas blasting nozzles 51 may be one or a plural. A gas or mist of a sterilizer or a mixture thereof blasted to the container 2 flows into the container 2, thus sterilizing the inner surface of the container 2. At this point of operation, the container 2 travels through the sterilizer gas blasting tunnel 64.

Accordingly, a gas or mist of a sterilizer or a mixture thereof also flows on the outer surface of the container 2 so that the outer surface of the container 2 is sterilized. It is also possible to adopt a configuration where the sterilizer gas blasting nozzle 51 follows the conveyed container 2, and is inserted into the container 2 so as to blast a gas or mist of a sterilizer or a mixture thereof to the inner surface of the container 2.

As a sterilizer blasted to the container 2 in the form of a gas, mist or a mixture of gas and mist, it is possible to use a sterilizer which is substantially equal to a sterilizer blasted to the preform 1 in the form of a gas, mist or a mixture of gas and mist. Further, a gas or mist of a sterilizer or a mixture thereof can be acquired by the sterilizer gas generator 48 shown in FIG. 5 in the same manner as the case of the preform 1. Further, generation conditions are also substantially equal to those in the case of the preform 1.

The blast amount of a gas or mist of a sterilizer or a mixture thereof is arbitrarily determined. The blast amount is determined according to the amount of sterilizer supplied to the sterilizer gas generator 48 and a blasting time. A plurality of sterilizer gas generators 48 may be provided. The blast amount varies also depending on the size of the container 2. A gas or mist of a sterilizer or a mixture thereof ejected from the sterilizer gas blasting nozzle 51 may be blasted to the container 2 in the state of being diluted with hot air.

In the case where hydrogen peroxide solution is used as a sterilizer, the blast amount of a gas of hydrogen peroxide solution is as follows. The amount of hydrogen peroxide adhering to the inner surface of the container 2 due to a gas of hydrogen peroxide solution blasted to the inner surface of the container 2 from the sterilizer gas blasting nozzle 51 is preferably set to a range from 0.01 $\mu$L/cm$^2$ to 0.1 $\mu$L/cm$^2$ in terms of hydrogen peroxide solution containing 35% by mass of hydrogen peroxide. It is more preferable to set the amount to 0.03 $\mu$L/cm$^2$ to 0.07 $\mu$L/cm$^2$. By setting the amount to 0.01 $\mu$L/cm$^2$ or more, it is possible to obtain a uniform sterilization effect for the entire container. Further, by setting the amount to 0.1 $\mu$L/cm$^2$ or less, a time of air rinsing for removing remaining hydrogen peroxide can be shortened so that such a value is economical. Further, the concentration of hydrogen peroxide in a gas or the like of hydrogen peroxide solution blasted to the container 2 is preferably set to 2 mg/L to 20 mg/L, and is more preferably set to 5 mg/L to 10 mg/L.

It is preferable that the container 2 to which a gas or mist of a sterilizer or a mixture thereof is blasted be conveyed to the air rinsing unit 32, and be rinsed with aseptic air. Aseptic air is blasted to the inner surface and the outer surface of the container 2 on an air rinsing wheel 34, and the container 2 is conveyed to the filling unit 37 through a wheel 36. The nozzle which blasts aseptic air to the inner surface of the container 2 may be provided so as to oppose the mouth portion 1*a* of the container 2. Alternatively, a nozzle which follows at the same speed as the conveyance of the container 2 may be inserted into the container 2. Further, a nozzle which is pointing the outer surface of the container 2 may be provided so as to blast aseptic air to the outer surface of the container 2. By performing air rinsing, it is possible to obtain an advantageous effect of activating a sterilizer blasted to the container 2, and an advantageous effect of removing the sterilizer blasted to the inner surface and foreign substance and dust which are present on the inner surface. Air used for air rinsing may be at a room temperature, or may be heated. However, performing air rinsing with heated air is more advantageous in activating a sterilizer. The temperature of aseptic air is preferably set to 40° C. to 170° C. When the temperature of aseptic air exceeds 170° C., the container 2 may be deformed. Air rinsing may be performed with the container 2 being brought into an upright position or an inverted position. To remove foreign substances, it is effective to perform air rinsing with the container 2 being brought into an inverted position. Further, to remove foreign substances, it is preferable to perform suction in the vicinity of the mouth portion 1*a* of the container 2 which is brought into an inverted position. It is preferable to set the amount of air blasted to one container to 2.5 L/container to 125 L/container.

The container 2 which is rinsed with aseptic air may be rinsed with aseptic water. By rinsing the container 2 with aseptic water, a sterilizer remaining in the container 2 is further removed. In the case where hydrogen peroxide solution is used as a sterilizer, it is possible to reduce the amount of hydrogen peroxide remaining in the container 2. Further, dust and foreign substances in the container 2 can be removed. In the case where the container 2 is rinsed with aseptic water, it is preferable to remove aseptic water by blasting aseptic air to the container 2. This is because there is a possibility that aseptic water adhering to the inner surface of the container 2 is mixed into contents.

A sterilizer in liquid form is blasted to the container 2 which is brought into an inverted position as shown in FIG. 14. To cause a sterilizer in liquid form to come into contact with the entire inner surface of the container 2, the sterilizer in liquid form is blasted to the inner surface of the container 2 from the mouth portion 1a by the sterilizer blasting nozzle 53a which is pointing upward in a state where the support ring 1b of the container 2 in an inverted position is held by the gripper 5. Further, a sterilizer in liquid form is blasted to the outer surface of the container 2 by the sterilizer blasting nozzle 53b which is pointing downward such that the sterilizer in liquid form comes into contact with the entire outer surface of the container 2. The sterilizer blasting nozzle 53a may be provided so as to oppose the mouth portion 1a of the container 2. Alternatively, a nozzle which follows at the same speed as the conveyance of the container 2 may be provided so as to be inserted into the container 2. The number of sterilizer blasting nozzles 53b may be a plural. Further, provided that a sterilizer in liquid form is allowed to come into contact with the inner and outer surfaces of the container 2, a method is not limited to that a sterilizer in liquid form is blasted by a nozzle, and the container 2 may be immersed in a sterilizer in liquid form. Further, mist of a sterilizer in liquid form may be blasted to the container 2 by a twin-fluid nozzle which supplies compressed air (0.2 MPa to 0.6 MPa) and a sterilizer in liquid form. Blasting of mist of a sterilizer in liquid form may be performed with the container 2 being brought into an upright position or an inverted position. Rinsing with aseptic water for removing a blasted sterilizer in liquid form from the container 2 is performed with the container 2 being brought into an inverted position. Further, it is also possible to adopt a configuration where the container 2 in an upright position is filled with a sterilizer in liquid form, and the container 2 is inverted, thus causing the sterilizer in liquid form to come into contact with the container 2.

As a sterilizer in liquid form, it is possible to use a sterilizer which is substantially equal to a sterilizer used for the preform 1. A sterilizer in liquid form is heated to 50° C. to 80° C., and is preferably heated to 60° C. to 70° C. Heating a sterilizer increases sterilization effect of the sterilizer. It is preferable to set the flow rate in one sterilizer blasting nozzle 53a and 53b to 1 L/min. to 15 L/min., and it is appropriate to set the flow rate to 3 L/min. to 10 L/min. Further, it is appropriate to set a blasting time to 0.2 seconds to 15 seconds. The blast amount of sterilizer in liquid form to the container 2 is determined according to the flow rate and the blasting time of the sterilizer blasting nozzles 53a and 53b. It is preferable to set the blast amount to 0.15 ml/cm$^2$ to 1.25 ml/cm$^2$ with respect to the surface area of the container 2. When the blast amount is less than 0.15 ml/cm$^2$, sterilization is not sufficiently performed. On the other hand, when the blast amount exceeds 1.25 ml/cm$^2$, sterilization is excessively performed, thus leading to waste of energy and a sterilizer.

The container 2 with which a sterilizer in liquid form is caused to come into contact is rinsed with aseptic water so as to remove a sterilizer adhering to the container 2. Rinsing of the container 2 with aseptic water is performed in the air rinsing unit 32 in FIG. 1 on the air rinsing wheel 34 by providing a nozzle. In the same manner as the case of the preform 1, aseptic water is produced by heating water for 4 minutes or more at 121.1° C. or above, or by causing water to pass through an aseptic filter. The container 2 is rinsed with aseptic water by steps and devices substantially equal to steps and devices used for blasting a sterilizer in liquid form to the container 2 shown in FIG. 14. To cause the entire inner surface of the container 2 to be rinsed with aseptic water, aseptic water is blasted to the inner surface of the container 2 from the mouth portion 1a by a nozzle which is pointing upward in a state where the support ring 1b of the container 2 in an inverted position is held by the gripper 5. Further, to cause the entire outer surface of the container 2 to be rinsed with aseptic water, aseptic water is blasted to the outer surface of the container 2 by a nozzle which is pointing downward. The nozzle which is pointing upward may be provided so as to oppose the mouth portion 1a of the container 2. Alternatively, it is also possible to adopt a configuration where a nozzle which follows at the same speed as the conveyance of the container 2 is provided, and the nozzle is inserted into the container 2. Further, the number of nozzles which point downward may be a plural.

Aseptic water is adjusted to 50° C. to 80° C., and preferably to 60° C. to 70° C. It is preferable to set the flow rate in one nozzle which blasts aseptic water to 3 L/min. to 15 L/min., and it is appropriate to set the flow rate to 5 L/min. to 10 L/min. Further, it is appropriate to set a blasting time to 0.2 seconds to 5 seconds. In the case where sterilization is performed only by blasting a sterilizer in liquid form to the container 2 without sterilizing the preform 1, it is necessary to blast the sterilizer in liquid form to the container 2 for a long time so that it is also necessary to perform rinsing with aseptic water for a long time. In such a case, it is necessary to perform rinsing for 5 seconds to 10 seconds. However, sterilizing the preform 1 can shorten a time during which rinsing is performed with aseptic water. The blast amount of aseptic water to the container 2 is determined according to the flow rate and the blasting time of the nozzle. It is preferable to set the blast amount to 0.15 ml/cm$^2$ to 1.25 ml/cm$^2$ with respect to the surface area of the container 2. When the blast amount is less than 0.15 ml/cm$^2$, rinsing is not sufficiently performed. On the other hand, when the blast amount exceeds 1.25 ml/cm$^2$, sterilization is excessively performed, thus leading to waste of energy. It is preferable that aseptic air be blasted to the container 2 to which aseptic water is blasted, thus removing aseptic water. This is because there is a possibility that aseptic water adhering to the inner surface of the container 2 is mixed into contents.

Irradiation of the container 2 according to the embodiment of the present invention with electron beam refers to irradiating the inner and outer surfaces of the conveyed container 2 with electron beam by the electron beam irradiation devices 54a, 54b and 54c in the same manner as the case where the preform 1 is irradiated with electron beam and in the same manner as the case shown in FIG. 6. The container 2 may be irradiated with electron beam from three directions in the same manner as FIG. 6. Any method may be adopted provided that the inner and outer surfaces of the container 2 are irradiated with electron beam. The thickness of the side surface of the container 2 is smaller than that of the preform 1. Accordingly, provided that electron beam emitted from the electron beam irradiation devices 54a and 54b have ability to pass through the side surface of the container 2, it is not always necessary to irradiate the inner surface of the container 2 with electron beam. However, the mouth portion 1a of the container 2 has a large thickness and hence, electron beam does not easily pass through the mouth portion 1a and hence, it is necessary to irradiate the inner surface of the mouth portion 1a with electron beam. Accordingly, by providing the electron beam irradiation device 54c or by providing a reflection mirror at a position above the mouth portion 1a, it is necessary to introduce electron beam emitted from the electron beam irradiation device 54a to the inner surface of the mouth portion 1a of the container 2. It is also possible to adopt a configuration where a magnetic device is provided so as to introduce electron beam emitted from the electron beam irradiation device 54a to the inner surface of the mouth portion 1a of the container 2. If the container 2 is rotated, it is sufficient to provide only the electron beam irradiation device 54a for irradiation from the side surface, and it is not always necessary to provide the electron beam irradiation device 54b. It is also possible to adopt a configuration where a rod-shaped electron beam irradiation device is inserted into the preform 1 so as to irradiate the inner surface of the preform 1 with electron beam.

It is preferable that foreign substances adhering to the inner and outer surfaces of the container 2 be removed before the container 2 is irradiated with electron beam. This method can be performed in the same manner as the method used for the preform 1. Further, it is preferable that the container 2 be rinsed with aseptic air after the container 2 is irradiated with electron beam. The reason is to remove ozone generated in the container 2 due to irradiation with electron beam. Such rinsing is performed by an aseptic air blasting nozzle provided to the air rinsing wheel 34 of the air rinsing unit 32 in FIG. 1.

Irradiation with light containing ultraviolet rays to the container 2 according to the embodiment of the present invention is performed in the same manner as the irradiation with light containing ultraviolet rays to the preform 1 shown in FIG. 7. As the light irradiation lamps 55 and the light reflecting plate 56, it is possible to use the light irradiation lamps and the light reflecting plate which are substantially equal to those used for the preform 1. Provided that the entire inner and outer surfaces of the container 2 are irradiated, the number of light irradiation lamps 55 is not limited. As shown in FIG. 7, a large number of light irradiation lamps 55 may be provided so as to irradiate the inner and outer surfaces of the container 2 with light containing ultraviolet rays. However, if the container 2 is rotated, the light irradiation lamps 55 which irradiate the side surface of the container 2 may be arranged in one row. To irradiate the inner surface of the container 2 with light containing ultraviolet rays, it is preferable that a rod-shaped light irradiation lamp be inserted into the container 2 so as to irradiate the inner surface of the container 2 with light containing ultraviolet rays. This is because even if the mouth portion 1a of the container 2 is irradiated with light containing ultraviolet rays, the light containing ultraviolet rays may not reach the inner surface of the barrel portion of the container 2 having a larger diameter than the mouth portion 1a.

It is preferable that foreign substances adhering to the inner and outer surfaces of the container 2 be removed before the container 2 is irradiated with light containing ultraviolet rays. This method can be performed in the same manner as the method used for the preform 1. Further, it is preferable that the container 2 be rinsed with aseptic air after the container 2 is irradiated with light containing ultraviolet rays. The reason is to remove ozone generated in the container 2 due to irradiation with light containing ultraviolet rays. Such rinsing is performed in the air rinsing unit 32 in FIG. 1 by an aseptic air blasting nozzle provided to the air rinsing wheel 34.

Contact of hot water with the container 2 according to the embodiment of the present invention is performed by blasting hot water to the inner and outer surfaces of the container 2 by a nozzle in the same manner as a step of blasting a sterilizer in liquid form to the container 2 which is brought into an inverted position as shown in FIG. 14. Hot water refers to aseptic water heated to 60° C. to 80° C. It is preferable to set the flow rate in one nozzle which blasts hot water to 1 L/min. to 15 L/min., and it is appropriate to set the flow rate to 3 L/min. to 10 L/min. Further, it is appropriate to set a blasting time to 0.2 seconds to 5 seconds. The blast amount of hot water to the container 2 is determined according to the flow rate and the blasting time of the nozzle. It is preferable to set the blast amount to 0.15 ml/cm$^2$ to 1.25 ml/cm$^2$ with respect to the surface area of the preform 1. When the blast amount is less than 0.15 ml/cm$^2$, sterilization is not sufficiently performed. On the other hand, when the blast amount exceeds 1.25 ml/cm$^2$, sterilization is excessively performed, thus leading to waste of energy.

It is preferable that hot water adhering to the container 2 sterilized with hot water is removed by blasting aseptic air to the inner and outer surfaces of the container 2. This is because there is a possibility that hot water is mixed into contents with which the container 2 is filled.

Figure 15:
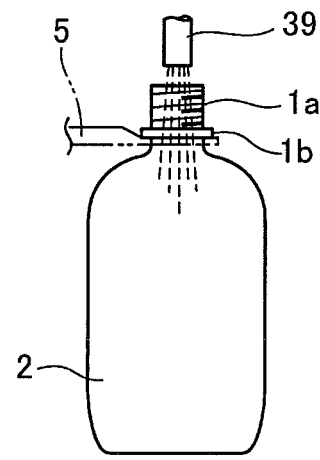
FIG. 15 shows a step of filling of the container with contents according to the embodiment of the present invention.
Figure 16:
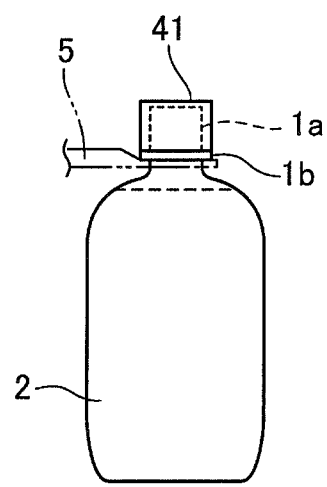
FIG. 16 shows a step of sealing the container according to the embodiment of the present invention.

Filling of the container 2 with heated contents according to the embodiment of the present invention refers to filling the container 2 with heated contents by a filling nozzle 39 provided to a filling wheel 40 in the filling unit 37 as shown in FIG. 15. The inner surface of the container 2 is sterilized by heat of the heated contents. The filling may be performed after the contents are cooled to a filling temperature following the contents are sterilized. Alternatively, it is also possible to adopt a configuration where contents are cooled once to a temperature near a room temperature after the contents are sterilized and, thereafter, the contents are heated to a filling temperature again. However, the method where contents are cooled to a filling temperature after the contents are sterilized is more preferable because the method consumes less energy. It is preferable to set the filling temperature to 60° C. to 70° C. The reason is as follows. The mouth portion 1a of the container 2 is not crystallized and hence, when the filling temperature exceeds 70° C., there is a possibility that the mouth portion 1a is deformed.

Filling with heated contents is performed in the filling unit 37. Accordingly, if a container sterilization step involves only filling with a heated content, the container sterilizing unit 30 and the air rinsing unit 32 are unnecessary. In the case where the container sterilization step involves filling with heated contents and another sterilization method in combination, the container sterilizing unit 30 and the air rinsing unit 32 are necessary depending on a sterilization method.

As described above, the container 2 is, in the container sterilizing unit 30, sterilized by performing any one, two or more selected from contact with a sterilizer, irradiation with electron beam, irradiation with light containing ultraviolet rays, contact with hot water, and filling with a heated content. Ability to sterilize the preform 1 and the container 2 within a range from the preform heating step to the container sterilization step is expressed by Y [LRV]. Sterilizing ability [LRV] is substantially equal to sterilizing ability in the sterilization step for the preform 1. Sterilizing ability within a range from the heating unit 12 for the preform 1 to the container sterilizing unit 30 is calculated as follows. The preform 1 to which indicator bacteria are caused to adhere is supplied to the wheel 9 to which the preform 1 is passed from a preform sterilizing wheel 7, the preform 1 is made to pass through the heating unit 12, the molding unit 17, the container sterilizing unit 30, and the air rinsing unit 32 and, in the filling unit 37, the container 2 is filled with a culture medium. Further, the container 2 which is discharged through the sealing unit 43 and the discharging unit 46 is cultured, and presence or absence of mortality of the indicator bacteria is checked, and sterilizing ability is calculated. For example, 1 g of indicator bacteria with $10^2$ [cfu/g] is caused to adhere to the inner surface of the preform 1, the container 2 which is discharged through respective steps of heating, molding, container sterilization, air rinsing, filling, and sealing is cultured. When the propagation of bacteria is not observed, sterilizing ability within a range from the heating step for the preform 1 to the sterilization step for the container 2 is 2 or more. By performing sterilization under conditions where various numbers of indicator bacteria are caused to adhere to the preform 1, Y [LRV] can be determined.

Y has to be zero or more. In the heating unit 12, the molding unit 17, the inspection wheel 23 and the atmosphere shut-off chamber 27 which are disposed downstream of a portion where preform sterilization is performed, there is a possibility that the preform 1 and the container 2 is contaminated with bacteria and the like. Accordingly, it is necessary to eliminate contaminated bacteria and the like at least in the sterilization step for the container 2. The reason is as follows. In the case where contaminated bacteria and the like cannot be eliminated in the sterilization step for the container 2, even if X is 6 or more, and X+Y exceeds 5, there is a possibility that a product which is to be filled with contents and to be discharged from the aseptic filling apparatus is not aseptic.

The container sterilizing unit chamber 31, the air rinsing unit chamber 33 and the filling unit chamber 38 are sterilized before the aseptic filling apparatus is operated. During the operation of the aseptic filling apparatus, aseptic air is supplied into each chamber, and is kept at a positive pressure. Accordingly, there is no possibility of contamination caused by bacteria and the like in each of these respective chambers.

Provided that X+Y is 5 or more and 10 or less, X may be 2 and Y may be 3, or X may be 4 and Y may be 1, for example. The reason X+Y is required to be set to 5 or more is that such a value is the reference of sterilizing ability which the aseptic filling apparatus is required to have as a level at which poor sterilization is not actually performed. Further, when X+Y exceeds 10, reliability of the aseptic filling apparatus is increased. However, there is no possibility that poor sterilization is actually performed, and the size of a facility becomes excessively large. Accordingly, a large burden of initial investment is imposed, and energy is consumed wastefully. By achieving a sterilization level which the aseptic filling apparatus is required to have by combining sterilization for the preform 1 and sterilization of the container 2, a facility can be made appropriate so that it is possible to suppress consumption of running energy. Further, it is possible to select whether sterilization of the preform 1 and sterilization of the container 2 are respectively performed by different sterilization methods or are performed by the same sterilization method and hence, selection range of a sterilization method can be expanded. For example, assume a case where sterilization of the preform 1 is performed by a method where a gas or mist of hydrogen peroxide or a mixture thereof is blasted to a container and sterilization of X=3 is performed, and sterilization of the container 2 is performed by a method where irradiation is performed with electron beam and a level of Y=2 is set. In such a case, both sterilizer apparatuses can be made light, and sterilizing ability of the aseptic filling apparatus can be made appropriate.

The container 2 which is air-rinsed in the air rinsing unit 32 is, as shown in FIG. 1, conveyed to the filling unit 37 through the wheel 36. In the filling unit 37, the container 2 is filled with sterilized contents by the filling nozzle 39 on the filling wheel 40 shown in FIG. 1 as in the filling step shown in FIG. 15. The filling nozzle 39 travels synchronously with the container 2 to fill the container 2 with a fixed amount of contents, such as a beverage.

The container 2 filled with contents is conveyed to the sealing unit 43 through a wheel 42 shown in FIG. 1. On a sealing wheel 44 provided to the sealing unit 43, as in the case of the sealing step shown in FIG. 15, the cap 41 sterilized in advance is screwed to the mouth portion 1a of the container 2 by a capper not shown in the drawing which is provided to the sealing wheel 44 so that the container 2 is sealed.

The sealed container 2 is passed to a gripper 5 of a discharging wheel 45 in the discharging unit 46 from the gripper 5 of the sealing wheel 44. The container 2 passed to the discharging wheel 45 is placed on the discharging conveyor 47. The container 2 placed on the discharging conveyor 47 is discharged to the outside of the aseptic filling apparatus from the inside of the filling unit chamber 38.

The present invention is not limited to the above-mentioned embodiment, and various modifications are conceivable. The method has been described where sterilizing ability X [LRV] in the preform sterilization step and sterilizing ability Y [LRV] within a range from the preform heating step to the container sterilization step are calculated such that the preform 1 to which indicator bacteria are caused to adhere is made to pass through the respective steps. It is also possible to adopt another method where, in the respective steps, the preform 1 and the container 2 are filled with a culture medium or a product solution, sterility assurance level (SAL) is calculated from defect rates of the preform 1 and the container 2, and obtained values are used as X and Y. Any method may be adopted provided that sterilizing ability can make bacteria and the like inactive. For example, disinfection is also included in a sterilizing ability.

1 . . . preform
2 . . . container
3 . . . cap
6 . . . preform sterilizing unit
12 . . . heating unit
17 . . . molding unit
24 . . . inspection device
30 . . . container sterilizing unit
32 . . . air rinsing unit
37 . . . filling unit
43 . . . sealing unit
46 . . . discharging unit
48 . . . sterilizer gas blasting nozzle
53 . . . sterilizer blasting nozzle 54 . . . electron beam irradiation device
55 . . . light irradiation lamp
57 . . . superheated steam generation device

The invention claimed is:

1. An aseptic filling method comprising:
a preform sterilization step where a preform is sterilized;
a preform heating step where the sterilized preform is heated to a molding temperature;
a molding step where the heated preform is molded into a container; a container sterilization step where the molded container is sterilized;
a filling step where the sterilized container is filled with sterilized contents in an aseptic atmosphere; and
a sealing step where the container filled with the contents is sealed by a sterilized lid member, the preform and the container being made to continuously travel,
wherein the preform heating step and the molding step are performed in a non-aseptic atmosphere,
wherein performing sterilizing ability in the preform sterilization step as X [LRV], and performing sterilizing ability within a range from the preform heating step to the container sterilization step as Y [LRV], with the sterilizing ability X [LRV] referring to ability to reduce a number of viable cells to $1/10^X$ and the sterilizing ability Y [LRV] referring to ability to reduce the number of viable cells to $1/10^Y$, Y is necessary to eliminate at least bacterial contaminants during a period of the heating step and the molding step, and the following formula is satisfied:

$5 \leq X+Y \leq 10$ (where $Y \geq 0$).

2. The aseptic filling method according to claim 1, wherein the preform sterilization step is performed by performing any one, two or more selected from contact of a sterilizer with the preform, irradiation with electron beam to the preform, irradiation with light containing ultraviolet rays to the preform, contact of hot water with the preform, and contact of superheated steam with the preform.

3. The aseptic filling method according to claim 1, wherein the container sterilization step is performed by performing any one, two or more selected from contact of a sterilizer with the container, irradiation with electron beam to the container, irradiation with light containing ultraviolet rays to the container, contact of hot water with the container, and filling of the container with heated contents.

4. An aseptic filling apparatus provided with a conveying path which causes a preform and a container to continuously travel until the preform is molded into the container, the container is filled with contents, and the container is sealed by a lid, the aseptic filling apparatus comprising:
a preform sterilizing device configured to sterilize the preform;
a heating unit configured to heat the sterilized preform to a molding temperature;
a molding unit configured to blow-mold the preform, which is heated to the molding temperature, into the container;
a container sterilizing device configured to sterilize the container which is blow molded;
a filling device configured to fill the sterilized container with sterilized contents; and
a sealing device configured to seal the container, which is filled with the contents, with a sterilized lid member, the preform sterilizing device, the heating unit, the molding unit, the container sterilizing device, the filling device, and the sealing device being provided along the conveying path,
wherein the heating unit and the molding unit are configured to be in a non-aseptic atmosphere,
wherein performing sterilizing ability of the preform sterilizing device as X [LRV], and performing sterilizing ability within a range from the heating unit to the container sterilizing device as Y [LRV], with the sterilizing ability X [LRV] referring to ability to reduce a number of viable cells to $1/10^X$ and the sterilizing ability Y [LRV] referring to ability to reduce the number of viable cells to $1/10^Y$, Y is necessary to eliminate bacterial contaminants at least in the heating unit and the molding unit, and the following formula is satisfied:

$5 \leq X+Y \leq 10$ (where $Y \geq 0$).

5. The aseptic filling apparatus according to claim 4, wherein the preform sterilizing device performs any one, two or more selected from contact of a sterilizer with the preform, irradiation with electron beam to the preform, irradiation with light containing ultraviolet rays to the preform, contact of hot water with the preform, and contact of superheated steam with the preform.

6. The aseptic filling apparatus according to claim 4, wherein the container sterilizing device performs any one, two or more selected from contact of a sterilizer with the container, irradiation with electron beam to the container, irradiation with light containing ultraviolet rays to the container, contact of hot water with the container, and filling of the container with heated contents.

* * * * *